(12) United States Patent
Yoon et al.

(10) Patent No.: US 11,932,639 B2
(45) Date of Patent: Mar. 19, 2024

(54) FUSED RING HETEROARYL COMPOUNDS AS ALK4/5 INHIBITORS

(71) Applicant: BiSiChem Co., Ltd., Seongnam (KR)

(72) Inventors: Cheolhwan Yoon, Seongnam (KR); Jonghwan Bae, Seongnam (KR); Cheolkyu Han, Seongnam (KR); Hongjun Kang, Seongnam (KR); Jeongbeob Seo, Seongnam (KR)

(*) Notice: Subject to any disclaimer, the term of this patent is extended or adjusted under 35 U.S.C. 154(b) by 0 days.

(21) Appl. No.: 16/749,306

(22) Filed: Jan. 22, 2020

(65) Prior Publication Data

US 2020/0231591 A1  Jul. 23, 2020

Related U.S. Application Data

(60) Provisional application No. 62/795,232, filed on Jan. 22, 2019.

(51) Int. Cl.
  *C07D 471/04*  (2006.01)
  *A61K 31/437*  (2006.01)

(52) U.S. Cl.
  CPC ................... *C07D 471/04* (2013.01)

(58) Field of Classification Search
  CPC ..... C07D 471/04; A61K 31/437; A61P 35/00; C12Q 1/005
  USPC ........... 514/303, 300; 546/119, 113; 435/184
  See application file for complete search history.

(56) References Cited

U.S. PATENT DOCUMENTS 8,080,568 B1 * 12/2011 Kim .................. A61P 1/18
                                                514/357

FOREIGN PATENT DOCUMENTS

WO   WO-2013002680 A2 *  1/2013  ........... B42D 25/324
WO   WO 2019/195248 A1 * 10/2019  ........... C07D 471/04

OTHER PUBLICATIONS

Cheng Hua Jin et al 4-([1,2,3]Triazolo[1,5-a]pyridine-6-yl)-5(3)-6(6-methylpyridin-2-yl)imidazole and pyrazole derivatives as potent and selective inhibitors of transforming growth factor-β type I receptor kinase. (Year: 2014).*
Chul-Yong Park et al EW-7195, a novel inhibitor. (Year: 2011).*
Rosendahl Alexander et al.Overactive Smad Signaling in Airway Inflammation. (Year: 2001).*

* cited by examiner

*Primary Examiner* — Charanjit Aulakh
(74) *Attorney, Agent, or Firm* — United One Law Group LLC; Kongsik Kim; Jhongwoo Peck

(57) ABSTRACT

The invention provides novel substituted heterocyclic compounds represented by Formula I, or a pharmaceutically acceptable salt, solvate, polymorph, ester, tautomer or prodrug thereof, and a composition comprising these compounds. The compounds provided can be used as inhibitors of ALK5 and/or ALK4 and are useful in the treatment of pulmonary fibrosis, NASH, obesity, diabetes, cancers and other inflammation.

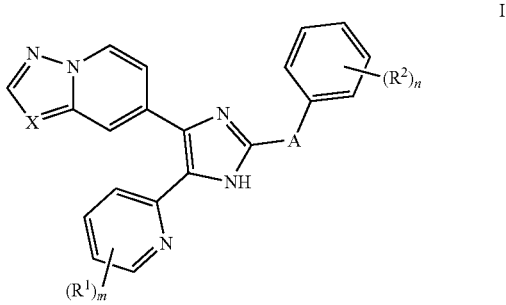

5 Claims, No Drawings

FUSED RING HETEROARYL COMPOUNDS AS ALK4/5 INHIBITORS

CROSS-REFERENCE TO RELATED APPLICATIONS

The present application claims priority to U.S. Provisional Application No. 62/795,232 filed on Jan. 22, 2019, which is incorporated herein by reference.

TECHNICAL FIELD

This invention relates to a series of substituted heterocyclic compounds which are inhibitors of the transforming growth factor-β (TGF-β) type I receptor (Activin Like Kinase5) and/or the activin type I receptor (ALK4) and are useful in the treatment of obesity, diabetes, glomerulonephritis, diabetic nephropathy, lupus nephritis, hypertension-induced nephropathy, renal interstitial fibrosis, renal fibrosis resulting from complications of drug exposure, HIV associated nephropathy, transplant nephropathy, liver fibrosis due to all etiologies, hepatic dysfunction attributable to infections, alcohol-induced hepatitis, NASH (non-alcoholic steatohepatitis), disorders of the biliary tree, pulmonary fibrosis, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, fibrotic cancers, tumor metastasis growth, radiation-induced fibrosis, and thrombosis. This invention also relates to a pharmaceutical composition comprising the compound of the invention, use of the compound in the preparation of a medicament, and method of treatment for hyperproliferative diseases in mammals, especially humans by administering the compound thereof.

BACKGROUND

Transforming growth factor-β (TGF-β) is a ubiquitously expressed, a potent pleiotropic cytokine that maintains physiological homeostasis by regulating cellular processes such as apoptosis, proliferation and differentiation.

The TGF-β superfamily represents a diverse set of growth factors, which signal through receptor serine/threonine kinases. The superfamily is subdivided into two branches: the TGF-β/Activin branch and the Bone Morphogenetic Protein (BMP)/Growth and Differentiation Factor (GDF) branch. Each branch is further divided into subgroups based on sequence similarity. The TGF-β/Activin branch includes TGF-β, Activin, Inhibin, Nodal, and Lefty ligands. The BMP/GDF branch includes BMP, GDF, and Mullerian Inhibitory Substance (MIS) ligands. Almost all cells secrete TGF-β and express TGF-β receptors.

Upon binding of active TGF-β to the ALK5 and type II (TGF-βRII) receptor, ALK5 is phosphorylates and activates by TGF-βRII. ALK5, in turn, phosphorylates and activates the R-Smads, Smad 2 and Smad 3, which form a complex with Smad 4. This complex translocates to the nucleus, which binds DNA in conjunction with other transcription factors and interacts with the general transcription machinery to regulate the expression of approximately 100-300 target genes.

Consistent with the many developmental defects that result from experimentally dysregulated TGF-β family signaling, moderate alterations in TGF-β family protein function have been linked to developmental syndromes and many diseases, including impaired wound healing, chronic fibrosis, cardiovascular diseases, obesity, diabetes and cancer.

TGF-β is heavily implicated in a variety of fibrous diseases (Border W A et al, N Engl J Med. 331(19):1286-1292 (1994)). Fibrosis occurs when there is an imbalance in extracellular matrix (ECM) deposition and degradation. Many TGF-β ligands are potent drivers of ECM deposition, and additionally, have natural affinity for the ECM, creating a concentrated pool of pro-fibrotic factors at the site of injury (Kelly L et al, Front in Pharm 8:461 (2017)). In response to injury, the influx of granulocytes, platelets, leukocytes, and additional parenchymal cells increase the presence of TGF-β at the site of the wound (Branton M H, et al, Microbes Infect. 1(15):1349-1365 (1999); Border W A et al, N Engl J Med. 331(19):1286-1292(1994)). TGF-β then induces fibroblast proliferation, myofibroblast differentiation, and remodeling of the extracellular matrix (Branton M H et al, Microbes Infect. 1(15):1349-1365 (1999); Border W A et al, N Engl J Med. 331(19):1286-1292(1994); Xiao L et al, Front Biosci. 17:2667-2674(2012); Roverts A B et al, Proc Natl Acad Sci USA. 83(12):4167-4171(1986)). Fibroblasts derived from hypertrophic scars have been shown to have an alteration in TGF-β signaling. Studies have indicated increased expression and phosphorylation of the Smads2 and/or 3 in hypertrophic scarring (Xie J L et al, Dermatol surg. 34(9):1216-1224 (2008); Kopp J et al, J Biol chem. 280(22):21570-6 (2005)). Activation of Smad 2/3 regulates to the expression of several profibrotic genes, including collagens [COL1A1, COL3A1, COL5A2, COL6A1, COL6A3, COL7A1] (Verrecchia F et al, J Biol chem. 276, 17058-17062 (2001)), plsminnogen activator inhibitor-1 (PAI-1) (Dennler S et al, EMBO J. 17:3091-3100 (1998); Hua X et al, Genes Dev. 12:3084-3095 (1998)), various proteoglycans (Schonherr E et al, J Biol Chem. 266:17640-17647 (1991); Romaris M et al, Biochem J. 310:73-81 (1995); Dadlani H et al, J Biol chem. 283:7844-7852 (2008)), integrin (Margadant C et al, EMBO Rep. 11:97-105 (2010)), connective tissue growth factor (Chen Y et al, Kidney Int. 62:1149-1159 (2002)), and matrix metalloproteases (MMPs) (Yuan W et al, J Biol Chem. 276:38502-38510 (2001)). Therefore, Neutralization of TGF-β in animal models inhibits liver fibrosis and reduces the risk of developing cholangiocarcinoma (Fan X et al, PLoS One. 8(12):82190 (2013); Ling H et al, PLoS One. 8(1):e54499 (2013)). ALK5 inhibitor inhibits the transcription and deposition of extracellular matrix and improves the deterioration of liver function in mice (Gouville A C et al, Br J Pharmacol. 145(2):166-77 (2005)). Based on previous reports, TGF-β signaling would appear to be a potential target for the prevention or treatment of fibrotic diseases. Thus, direct inhibition of ALK5 represents an attractive way to prevent detrimental profibrotic effects of TGF-β. Recently described synthetic inhibitors of ALK5 have been shown to block TGF-β effects in cellular assays (Callahan J F et al, J Med Chem. 45:999-1001 (2002); Inman G et al, Mol Pharmacol. 62:65-74 (2002); Laping N et al, Mol Pharmacol. 62:58-64 (2002); Sawyer J S et al, J Med Chem. 46:3953-3956 (2003)).

Recent findings on the role of TGF-β signaling via ALK5 in the pathogenesis of obesity and type 2 diabetes have underscored its importance in metabolism and adiposity. Indeed, elevated TGF-β has been previously reported in human adipose tissue during morbid obesity and diabetic neuropathy. In vivo findings on the role of TGF-β signaling in metabolism based on the studies using Smad 3-knockout (Smad $3^{-/-}$) mice. TGF-β signaling via ALK5 regulates insulin gene transcription in the pancreatic islet β-cells (Lin H M et al, J Biol Chem. 284:12246-12257 (2009)), whereas Smad 3 deficiency in mice protects against insulin resistance and type 2 diabetes during high-fat diet-induced obesity (Tan C K et al, Diabetes 60:464-476 (2011); Yadav H et al, Cell Metab. 14:67-79 (2011)). These Smad $3^{-/-}$ mice exhibited diminished adiposity with improved glucose tolerance and insulin sensitivity. These mutant mice also displayed increased β-oxidation in the adipose tissue upon administration of a high-fat diet, thus ameliorating gluco- and lipotoxicity in the pancreas, skeletal muscle and liver by preventing ectopic fat accumulation (Tan C K et al, Diabetes. 60:464-476 (2011)). Notably, when TGF-β signaling was blocks phosphorylation of Smad 3 by treatment with a TGF-β neutralizing antibody, it protected the mice from obesity and type 2 diabetes (Yadav H et al, Cell Metab. 14:67-79 (2011)). Small molecule inhibitors of the TGF-β signaling via ALK5 promote β-cell replication in human islets transplanted into NOD-scid IL-2Rgnull mice (Dhawan S et al, Diabetes. 65(5):1208-1218 (2016)). These findings indicate that Smad 3, the canonical intracellular mediator of TGF-β/ALK5, serves as a multifaceted regulator of metabolic homeostasis, thus identifying ALK5 mediated Smad 3 phosphrylation as a potential target in the treatment of obesity and its associated disorders.

Overexpression of and/or defects in TGF-β signaling have been linked to many cancers, including lung, pancreatic, colon, prostate, and breast cancer (Eliott R L et al, J din Oncol. 23:2078-2093 (2005)). Through these studies, it has become clear that TGF-β can function as both a tumor suppressor and a tumor promoter (Akhurst R J et al, Trends Cell Biol. 11(11):44-51 (2011)). In benign epithelia and many early-stage tumors, TGF-β is a potent inducer of growth arrest. However, in advanced tumors, TGF-β signaling pathways are severely dysregulated. Rather than inhibiting carcinogenesis, TGF-β promotes tumor growth and progression at late stages (Akhurst R J et al, Trends Cell Biol. 11(11):S44-51 (2011); Massague J et al, Cell. 134(2): 215-230 (2008); Padua D et al, Cell Res. 19(1):89-102 (2009); Inman G J et al, Curr Opin Genet Dev. 21(1):93-99 (2011); Pasche B et al, J Cell Physio.l 186(2):153-168 (2001); Langenskiold M et al, J Surg Oncol. 97(5):409-415 (2008)). This functional switch is known as the TGF-β paradox. There is also evidence that the tumor suppressor versus oncogenic effects of TGFβ are contextual and/or depend on the temporal stage of cellular transformation. For example, the expression of ALK5 mutant that is unable to bind Smad 2/3 results in larger, more proliferative, less differentiated mammary tumors. However, expression of the same mutant in highly malignant mammary cells suppresses their ability to metastasize to the lungs (Tian F et al, Cancer Res. 64:4523-30 (2004)).

The pluripotent nature of TGF-β provides both opportunities and challenges to neutralize its effects. However, many cancers often become refractory to this growth inhibition either due to genetic loss of TGF-β signaling components or, more commonly, because of downstream perturbation by other integrated signaling pathways. During this time, the protumorigenic actions of TGF-β may prevail, including immunomodulatory properties, induction of angiogenesis and/or promotion of the epithelial-to-mesenchymal transition (EMT) facilitating cancer migration and invasion.

TGF-β has an adverse effect on anti-tumor immunity and significantly inhibits host tumor immune surveillance. TGF-β plays a crucial role in the repression of the immune system, as attested by the gross autoimmunity developed in TGF-β1 null mice (Shull M M et al, Nature. 359(6397): 693-699 (1992)). Interestingly, this T-cell-specific blockade of TGF-β signaling allows the generation of tumor-specific cytotoxic T lymphocytes (CTLs) that are capable of eradicating tumors in mice challenged with EL-4 thymoma or B16-F10 melanoma tumor cells (Thomas D A et al, Cancer Cell. 8(5):369-380 (2005)). TGF-β also has a significant impact on CD4+ T-cell differentiation and function and inhibits NK-cell proliferation and function, which is in part modulated by CD4+CD25+ regulatory T cells that are known to produce high levels of TGF-β (Nakamura et al, J Exp Med. 194(5):629-644 (2001); Ghiringhelli F et al, J Exp Med. 202(8):1075-1085 (2005); Shevach E M et al, Immunity. 30(5):636-645 2009)).

A prior study suggested the roles of TGF-β signaling in angiogenesis. Inhibiting TGF-β signaling through ALK5 results in increased endothelial cell (EC) migration and proliferation, which are further enhanced in the presence of vascular endothelial growth factor (VEGF) (Liu Z et al, J Cell Sci. 122:3294-3302 (2009)). ECs have been reported to express two distinct ALK5 and ALK1. The importance of these two receptors in mediating vessel development by TGF-β is evidenced by the embryonic lethality observed at day E11.5 and E10.5 in mice lacking ALK1 (Oh S P et al, Proc Natl Sci USA. 97:2626-2631 (2000)) or ALK5 (Larsson J et al, EMBO J. 20:1663-1673 (2001)), respectively. The canonical SMAD2/3 pathway is activated by ALK5, inducing the expression of PAI-1 and fibronectin, thereby impeding angiogenesis (Goumans M J et al, Mol Cell. 12:817-828 (2003); Goumans M J et al, EMBO J. 21:1743-1753 (2002); Wu X et al, Microvasc Res. 71:12-19 (2006); Ota T et al, J Cell Physiol. 193:299-318 (2002); Safina A et al, Oncogene 26(17):2407-22 (2007)). EMT also is marked by the loss of E-cadherin and the expression of mesenchymal proteins such as vimentin, fibronectin, and N-cadherin, facilitating the invasion process and worsening prognosis. In cancer cells, the repression of E-cadherin and the induction of vimentin, matrix-metalloproteinases (MMPs), and other pro-EMT factors can be drive by TGF-β (Lee J M et al, J Cell Biol. 172(7):973-981 (2006); Zhao Y et al, Cell Biochem Funct. 26(5):571-577 (2008)).

The extensive knowledge surrounding TGF-β-mediated, ALK5-dependent signaling and Smad 2/Smad 3 phosphorylation as a proximal event at the heteromeric receptor complex has focused initial drug discovery efforts on the type I receptor kinase as a therapeutic target (Laping N J et al, Curr Opin Pharm. 3:204-208 (2003); Singh J et al, Curr Opin Drug Disc Dev. 7:437-445 (2004)). SB-505124, a competitive inhibitor of the ATP-binding site of ALK5, diminishes growth in KRAS-driven pancreatic cancer cells that lack Rb (Gore et al, J Cli Invest. 124(1):338-352 (2014)). LY2157299 (Galunisertib), an oral small molecule inhibitor of the ALK5 that specifically downregulates the phosphorylation of Smad 2, abrogating activation of the canonical pathway. LY2157299 is currently in early clinical trials for the treatment of advanced, metastatic cancers (Herbertz et al, Drug Des Devel Ther. 10(9):4479-4499 (2015)). TEW-7197, a small molecule inhibitor of ALK5 for anti-Multiple myeloma therapy, is being evaluated in phase I clinical trials in patients with solid tumors (NCT02160106).

SUMMARY

This invention provides a compound of formula I, or a pharmaceutically acceptable salt, solvate, polymorph, ester, tautomer or prodrug thereof:

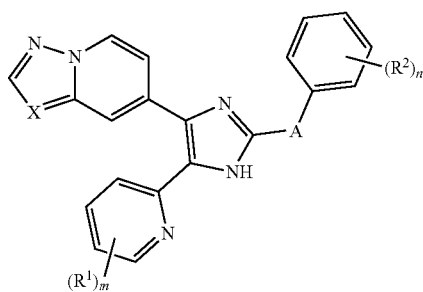

I wherein
each $R^1$ is independently selected from the group consisting of hydrogen, halogen, $CF_3$, acyl, amino, substituted amino, C1-C6alkyl, substituted C1-C6alkyl, C1-C6haloalkyl, C3-C7cycloalkyl, alkylcarboxy, cyano, nitro, alkoxy;
each $R^2$ is independently selected from the group consisting of hydrogen, halogen, $CF_3$, acyl, amino, substituted amino, C1-C6alkyl, substituted C1-C6alkyl, C1-C6haloalkyl, cyano, nitro, alkoxy, acyloxy, aryloxy;
m is 0, 1, 2, 3 or 4;
n is 0, 1, 2, 3, 4 or 5;
X is CH or N;
A is —$CH_2Y$—, —$CHR^3Y$—, —$CR^3R^4Y$—, —C(O) Y—, —$YCH_2$—, —$YCHR^3$—, —$YCR^3R^4$—, —YC(O)—,
Y is NH, $NR^5$, O, S, S(O) or $S(O)_2$;
$R^3$ is selected from the group consisting of F, $CF_3$, C1-C6alkyl, substituted C1-C6alkyl, cyano;
or $R^3$ and $R^4$ together with the atom to which they are attached form a 3 to 7 membered carbocyclic or heterocyclic ring;
$R^4$ is F, $CF_3$, C1-C6 alkyl;
$R^5$ is C1-6Calkyl, C1-6Cfluoroalkyl, C1-6Cdifluoroalkyl, C1-6Ctrifluoroalkyl;

Compounds of Formula I further include the absolute configuration compounds of Formula IIa and IIb.

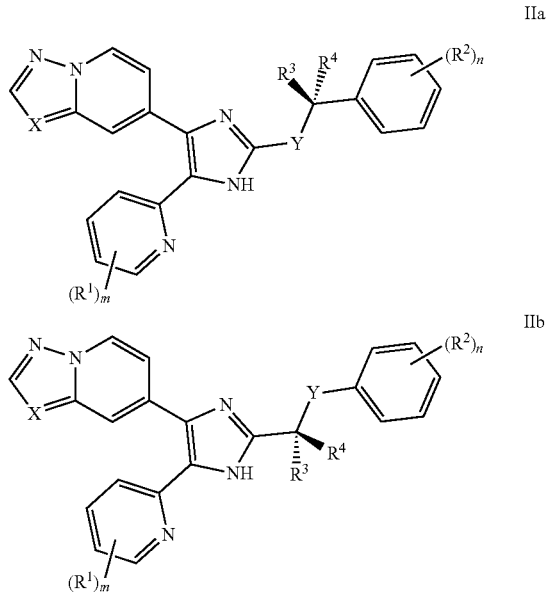

or salt thereof, wherein;
each $R^1$ is independently selected from the group consisting of hydrogen, halogen, $CF_3$, acyl, amino, substituted amino, C1-C6alkyl, substituted C1-C6alkyl, C1-C6haloalkyl, C3-C7cycloalkyl, alkylcarboxy, cyano, nitro, alkoxy;
each $R^2$ is independently selected from the group consisting of hydrogen, halogen, $CF_3$, acyl, amino, substituted amino, C1-C6alkyl, substituted C1-C6alkyl, C1-C6haloalkyl, cyano, nitro, alkoxy, acyloxy, aryloxy;
$R^3$ is selected from the group consisting of F, $CF_3$, C1-C6alkyl, substituted C1-C6alkyl, cyano;
or $R^3$ and $R^4$ together with the atom to which they are attached form a 3 to 7 membered carbocyclic or heterocyclic ring;
$R^4$ is F, $CF_3$, $C_1$-$C_6$ alkyl;
Y is NH, $NR^5$, O, S, S(O) or $S(O)_2$;
m is 0, 1, 2, 3 or 4;
n is 0, 1, 2, 3, 4 or 5;
$R^5$ is C1-6Calkyl, C1-6Cfluoroalkyl, C1-6Cdifluoroalkyl, C1-6Ctrifluoroalkyl;

Compounds of present invention are inhibitors of the transforming growth factor-β (TGF-β) type I receptor (ALK5) and/or the activin type I receptor (ALK4) and, consequently, are useful for treating pulmonary fibrosis, obesity, diabetes, NASH (non-alcoholic steatohepatitis), cancers and other inflammation.

In other aspects, the present invention is directed to a pharmaceutical composition comprising an effective amount of a compound of formula I or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of a compound of formula I or a pharmaceutically acceptable salt, solvate, polymorph, ester, tautomer or prodrug thereof.

In other aspects, the present invention is directed to a method of treating an obesity, diabetes, NASH (non-alcoholic steatohepatitis), cancer, liver fibrosis due to all etiologies, renal interstitial fibrosis, pulmonary fibrosis, inflammation, certain infectious diseases, condition, or disorder in a mammal, including a human, comprising administering to said mammal a therapeutically effective amount of a compound of formula I, or a pharmaceutically acceptable salt, ester, prodrug, solvate, such as hydrate, polymorph or tautomer thereof.

In other aspects, the present invention is directed to a method of treating a disorder or condition which is modulated by the transforming growth factor-$\beta$ (TGF-$\beta$) type I receptor (ALK5) and/or the activin type I receptor (ALK4) cascade in a mammal, including a human, comprising administering to said mammal an amount of the compound of formula I, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the ALK cascade in a mammal, including a human. The pharmaceutical composition is useful for treating pulmonary fibrosis, obesity, diabetes, cancers and other inflammation.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments, the amount of compound of formula I is in the range of about 0.001 to about 1000 mg/kg body weight/day. In further or additional embodiments, the amount of compound of formula I is in the range of about 0.5 to about 50 mg/kg body weight/day.

In other aspects, the present invention is directed to a process for preparing a compound of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$, ... $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "C1-C6 alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2 π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

Certain Pharmaceutical Terminology

The term "ALK inhibitor" as used herein refers to a compound that exhibits an $IC_{50}$, with respect to ALK activity, of no more than about 100 μM or not more than about 50 μM, as measured in the kinase assay described generally herein. "$IC_{50}$" is that concentration of inhibitor which reduces the activity of an enzyme to half-maximal level. Compounds described herein have been discovered to exhibit inhibition against ALK. Compounds of the present invention preferably exhibit an $IC_{50}$ with respect to ALK of no more than about 10 μM, more preferably, no more than about 5 μM, even more preferably not more than about 1 μM, and most preferably, not more than about 200 nM, as measured in the kinase assay described herein.

The term "selective," "selectively," or "selectivity" as used herein refers to a compound of this invention having a lower $IC_{50}$ value for the enzyme as compared to any other enzymes (e.g., at least 2, 5, 10 or more-fold lower).

The term "subject", "patient" or "individual" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19.). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and*

Development, Krosgaard-Larsen and H. Bundgaard, Ed., 1991, Chapter 5, p. 113-191; and Bundgaard, H., *Advanced Drug Delivery Review,* 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics,* 9th Edition, McGraw-Hill (1996).

Experimental Part

NMR spectra were recorded in $CDCl_3$ and $DMSO-d_6$ solution in 5-mm o.d. tubes (Norell, Inc. 507-HP) at 25° C. and were collected on Varian VNMRS-400 at 400 MHz for $^1H$. The chemical shifts ($\delta$) are relative to tetramethylsilane (TMS=0.00 ppm) and expressed in ppm. LC/MS was taken on Ion-trap Mass Spectrometer on FINNIGAN Thermo LCQ Advantage MAX, Agilent LC 1200 series (Column: YMC Hydrosphere (C18, Ø4.6×50 mm, 3 μm, 120 Å, 40° C.) operating in ESI(+) ionization mode; flow rate=1.0 mL/min. Mobile phase=0.01% heptafluorobutyric acid (HFBA) and 1.0% isopropyl alcohol (IPA) in water or $CH_3CN$.

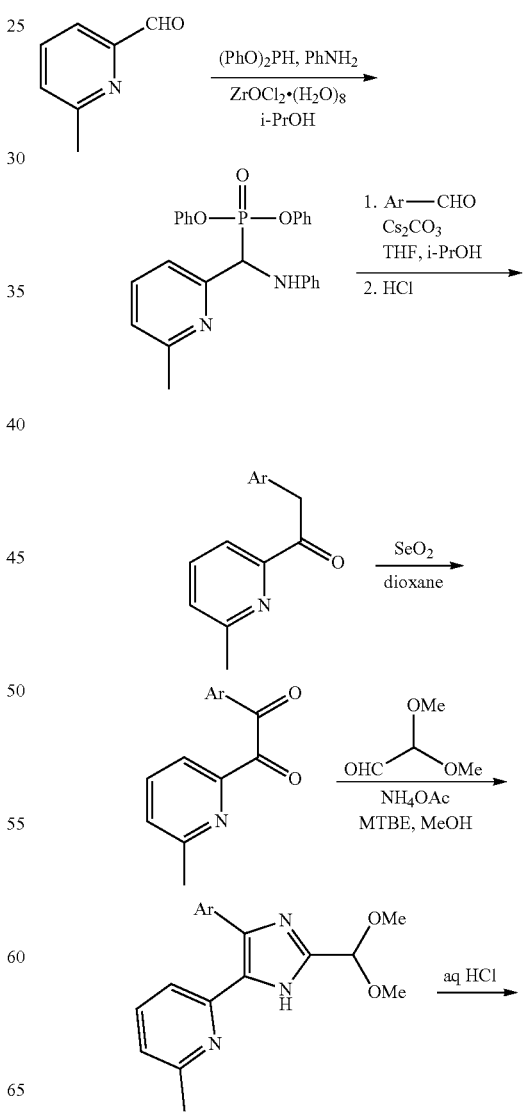

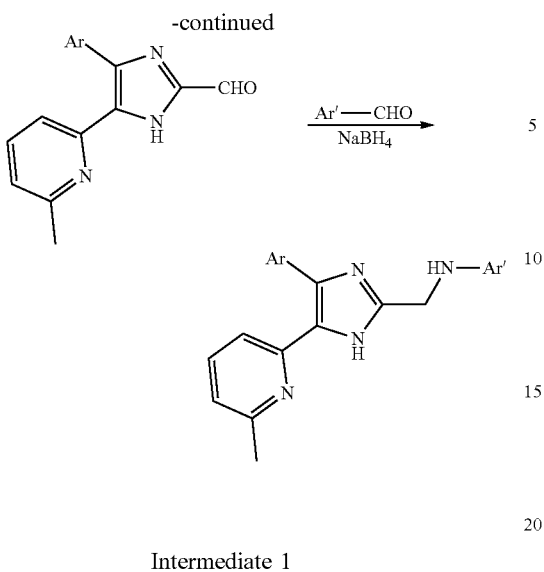

Intermediate 1 pyrazolo[1,5-a]pyridine-5-carbaldehyde

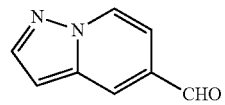 [SMILES: O=Cc1ccn2nccc2c1]

Step A: 1-amino-4-(hydroxymethyl)pyridinium 2,4,6-trimethylbenzenesulfonate

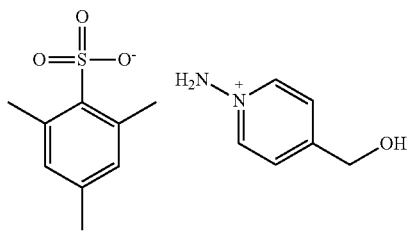

To a solution of (Z)-ethyl N-mesitylsulfonyloxyacetimidate (1.96 g, 6.87 mmol) in dioxane (4.0 mL) was added HClO$_4$ (70 wt % solution in water, 0.717 mL, 8.43 mmol) at 0° C. The mixture was stirred at 0° C. for 30 minutes and treated with ice-water. A precipitated solid was collected to afford O-(methylsulfonyl)hydroxylamine as a white solid, which was dissolved in DCM (21 mL), dried over Na$_2$SO$_4$, and filtered to afford a solution of O-(methylsulfonyl)hydroxylamine in DCM. The solution was added to a solution of pyridine-4-ylmethanol (500 mg, 4.58 mmol) in DCM (21 mL) at room temperature. The reaction mixture was stirred at room temperature for 6 hours and then concentrated in vacuo. The residual solid was suspended in diethyl ether, collected by filtration, washed with diethyl ether, and dried under vacuum to afford 1-amino-4-(hydroxymethyl)pyridinium 2,4,6-trimethylbenzenesulfonate (1.49 g, 100%) as a yellow solid. MS: 124.99 [M+H]$^+$ Step B: ethyl 5-(hydroxymethyl)pyrazolo[1,5-a]pyridine-3-carboxylate

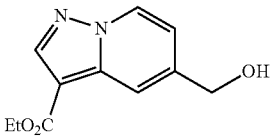

To a solution of 1-amino-4-(hydroxymethyl)pyridinium 2,4,6-trimethylbenzenesulfonate (1.49 g, 4.59 mmol) in DMF (15 mL) was added K$_2$CO$_3$ (1.27 g, 9.16 mmol) and ethyl propiolate (541 mg, 5.51 mmol) at room temperature. The reaction mixture was stirred at room temperature for 18 hours. After quenched with water, the mixture was extracted with EtOAc twice. The combined organic layers were dried over Na$_2$SO$_4$, filtered and concentrated in vacuo. The residue was purified by column chromatography on SiO$_2$ (Hexanes:EtOAc=1:5 to 3:2) to afford ethyl 5-(hydroxymethyl)pyrazolo[1,5-a]pyridine-3-carboxylate (398 mg, 39%) as a brown solid. $^1$H-NMR (400 MHz, CDCl$_3$): δ 8.46 (1H, d, J=7.2 Hz), 8.37 (1H, s), 8.09 (1H, s), 6.97 (1H, dd, J=7.4, 1.8 Hz), 4.81 (2H, d, J=4.8 Hz), 4.38 (2H, q, J=7.2 Hz), 1.41 (3H, t, J=6.8 Hz).

Step C: pyrazolo[1,5-a]pyridin-5-ylmethanol

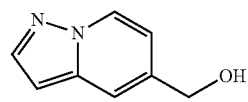 [SMILES: OCc1ccn2nccc2c1]

A solution of ethyl 5-(hydroxymethyl)pyrazolo[1,5-a]pyridine-3-carboxylate (398 mg, 1.81 mmol) in H$_2$SO$_4$ (40% solution of water, 12 mL) was heated at 110° C. for 6 hours and cooled to room temperature. After neutralization with 5 N aq. NaOH, the mixture was extracted with DCM twice. The combined organic layers were dried over Na$_2$SO$_4$, filtered and concentrated in vacuo. The residue was purified by column chromatography on SiO$_2$ (EtOAc only) to afford pyrazolo[1,5-a]pyridin-5-ylmethanol (176 mg, 66%) as a colorless oil. $^1$H-NMR (400 MHz, DMSO-d$_6$): δ 8.58 (1H, d, J=7.2 Hz), 7.92 (1H, d, J=2.4 Hz), 7.53 (1H, s), 6.77 (1H, dd, J=7.0, 1.4 Hz), 6.51 (1H, d, J=2.0 Hz), 5.39 (1H, t, J=5.8 Hz), 4.50 (2H, d, J=5.6 Hz).

Step D: pyrazolo[1,5-a]pyridine-5-carbaldehyde

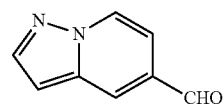 [SMILES: O=Cc1ccn2nccc2c1]

To a solution of pyrazolo[1,5-a]pyridin-5-ylmethanol (176 mg, 1.19 mmol) in DCM (12 mL) was added MnO$_2$ (1.03 g, 11.9 mmol) at room temperature. The reaction mixture was stirred at room temperature for 18 hours. After filtration through a Celite pad, the filtrate was concentrated in vacuo to afford pyrazolo[1,5-a]pyridine-5-carbaldehyde (153 mg, 88%) as a white solid. $^1$H-NMR (400 MHz, DMSO-d$_6$): δ 10.0 (1H, s), 8.80 (1H, d, J=7.2 Hz), 8.46 (1H, s), 8.19 (1H, d, J=2.4 Hz), 7.20 (1H, dd, J=7.2, 1.6 Hz), 7.05 (1H, d, J=2.0 Hz).

Intermediate 2

[1,2,4]triazolo[1,5-a]pyridine-7-carbaldehyde

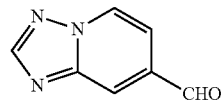 [SMILES: O=Cc1ccn2ncnc2c1]

Step A: (E)-N'-hydroxy-N-(4-(hydroxymethyl)pyridin-2-yl)formimidamide

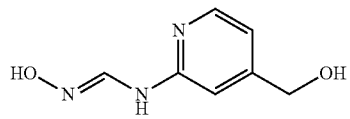 [SMILES: OCc1ccnc(N/C=N/O)c1]

To a solution of (2-aminopyridin-4-yl)methanol (500 mg, 4.03 mmol) in i-PrOH (10 mL) was added DMF-DMA (1.62 mL, 12.1 mmol) at room temperature. The mixture was stirred at 90° C. for 3 hours under N$_2$ and cooled to 50° C. After addition of hydroxylamine hydrochloride (840 mg, 12.1 mmol), the resulting reaction mixture was stirred at 50° C. overnight. After concentration in vacuo, the residue was purified by column chromatography SiO$_2$ (Hexanes:EtOAc=1:9) to afford (E)-N'-hydroxy-N-(4-(hydroxymethyl)pyridin-2-yl)-formimidamide (415 mg, 62%) as a yellow solid. $^1$H-NMR (400 MHz, DMSO-d$_6$): δ 9.98 (1H, s), 9.26 (1H, d, J=9.6 Hz), 8.02 (1H, d, J=5.2 Hz), 7.82 (1H, d, J=9.6 Hz), 6.99 (1H, s), 6.75 (1H, d, J=5.2 Hz), 5.32 (1H, t, J=5.2 Hz), 4.40 (2H, d, J=5.2 Hz).

Step B: [1,2,4]triazolo[1,5-a]pyridin-7-ylmethanol

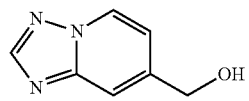 [SMILES: OCc1ccn2ncnc2c1]

To a solution of (E)-N'-hydroxy-N-(4-(hydroxymethyl)pyridin-2-yl)formimidamide (415 mg, 2.48 mmol) in THF (12 mL) was added TFAA (382 μL, 2.73 mmol) at 0° C. The reaction mixture was stirred at room temperature for 3 hours under N$_2$. After neutralization with saturated aq. NaHCO$_3$ at 0° C., the mixture was stirred at room temperature for 30 minutes and then concentrated in vacuo. The residue was purified by column chromatography on NH—SiO$_2$ (EtOAc:MeOH=99:1) to afford [1,2,4]triazolo[1,5-a]pyridin-7-ylmethanol (250 mg, 67%) as a white solid. $^1$H-NMR (400 MHz, DMSO-d$_6$): δ 8.87 (1H, d, J=6.4 Hz), 8.44 (1H, s), 7.69 (1H, s), 7.12 (1H, d, J=6.8 Hz), 5.59 (1H, t, J=5.2 Hz), 4.64 (2H, d, J=5.2 Hz).

Step C: [1,2,4]triazolo[1,5-a]pyridine-7-carbaldehyde

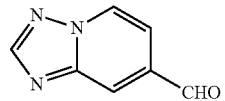 [SMILES: O=Cc1ccn2ncnc2c1]

To a solution of (COCl)$_2$ (264 μL, 3.02 mmol) in DCM (10 mL) was added DMSO (333 μL, 4.69 mmol) at −78° C. The mixture was stirred at −78° C. for 30 minutes. After addition of [1,2,4]triazolo[1,5-a]pyridin-7-ylmethanol (250 mg, 1.68 mmol), the reaction mixture was stirred at −78° C. for 90 minutes and then treated with TEA (929 μL, 6.70 mmol). The mixture was warmed to room temperature and quenched with water. The separated aqueous layer was extracted with DCM twice. The combined organic layers were dried over Na$_2$SO$_4$, filtered and concentrated in vacuo. The residue was purified by column chromatography on SiO$_2$ (Hexanes:EtOAc=1:9) to afford [1,2,4]triazolo[1,5-a]pyridine-7-carbaldehyde (181 mg, 73%) as a yellow solid. $^1$H-NMR (400 MHz, CDCl$_3$): δ 10.13 (1H, s), 8.72 (1H, d, J=7.2 Hz), 8.52 (1H, s), 8.28 (1H, s), 7.57 (1H, dd, =7.2, 1.6 Hz).

Intermediate 3

5-(6-emthylpyridin-2-yl)-4-(pyrazolo[1,5-a]pyridin-5-yl)-1H-imidazole-2-carbaldehyde

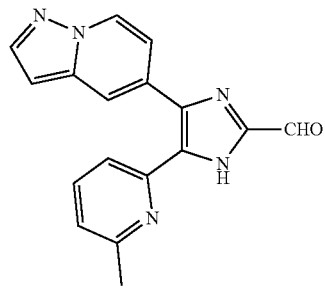 [SMILES: Cc1cccc(-c2[nH]c(C=O)nc2-c2ccn3nccc3c2)n1]

Step A: diphenyl (6-methylpyridin-2-yl)(phenylamino)methylphosphonate

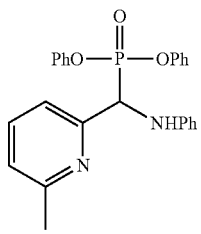

A mixture of 6-methylpicolinaldehyde (1.00 g, 8.26 mmol), diphenyl phosphite (1.92 mL, 9.91 mmol), aniline (754 μL, 8.26 mmol) and ZrOCl$_2$8H$_2$O (266 mg, 0.826 mmol) in i-PrOH (16 mL) was stirred at room temperature for 2 hours. The reaction mixture was quenched with water and then extracted with DCM twice. The combined organic layers were dried over Na₂SO₄, filtered and concentrated in vacuo. The residue was purified by column chromatography on SiO₂ (Hexanes:EtOAc=7:3 to 3:2) to afford diphenyl (6-methylpyridin-2-yl)(phenylamino)methylphosphonate (3.67 g, quant.) as a yellow solid. ¹H-NMR (400 MHz, CDCl₃): δ 7.51 (1H, t, J=7.6 Hz), 7.35 (1H, d, J=7.6 Hz), 7.25-7.23 (4H, m), 7.21-7.10 (4H, m), 7.08-7.00 (4H, m), 6.78-6.73 (3H, m), 5.48 (1H, t, J=7.6 Hz), 5.32 (1H, dd, J=21.0, 8.0 Hz), 2.52 (3H, s).

Step B: 1-(6-methylpyridin-2-yl)-2-(pyrazolo[1,5-a]pyridin-5-yl)ethanone

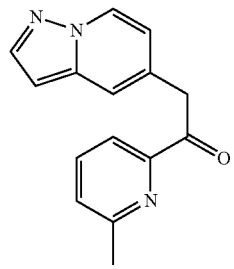 [SMILES: Cc1cccc(C(=O)Cc2ccn3nccc3c2)n1]

A mixture of diphenyl (6-methylpyridin-2-yl)(phenylamino)methylphosphonate (451 mg, 1.05 mmol), pyrazolo[1,5-a]pyridine-5-carbaldehyde (Intermediate 1, 153 mg, 1.05 mmol) and Cs₂CO₃ (444 mg, 1.36 mmol) in a mixture of THF (4.9 mL) and IPA (1.2 mL) was stirred at room temperature for 18 hours. After addition of 2 N aq. HCl (4.0 mL, 8.0 mmol), the resulting reaction mixture was stirred at room temperature for an additional 1 hour and cooled to ° C. After neutralization with saturated aq. NaHCO₃ at 0° C., the mixture was extracted with DCM twice. The combined organic layers were dried over Na₂SO₄, filtered, and concentrated in vacuo. The residue was purified by column chromatography on SiO₂ (Hexanes:EtOAc=1:1) to give 1-(6-methylpyridin-2-yl)-2-(pyrazolo[1,5-a]pyridin-5-yl)ethanone (178 mg, 68%) as a yellow solid. ¹H-NMR (400 MHz, DMSO-d₆): δ 5.58 (1H, d, J=7.2 Hz), 7.93 (1H, d, J=2.0 Hz), 7.89 (1H, t, J=7.6 Hz), 7.78 (1H, d, J=7.6 Hz), 7.54 (2H, d, J=7.6 Hz), 6.78 (1H, dd, J=7.2, 1.6 Hz), 6.50 (1H, d, J=2.0 Hz), 4.56 (2H, s), 2.60 (3H, s).

Step C: 1-(6-methylpyridin-2-yl)-2-(pyrazolo[1,5-a]pyridin-5-yl)ethane-1,2-dione

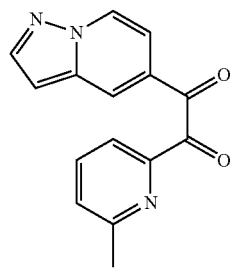

To a solution of 1-(6-methylpyridin-2-yl)-2-(pyrazolo[1,5-a]pyridin-5-yl)ethanone (178 mg, 0.708 mmol) in dioxane (7.1 mL) was added selenium dioxide (118 mg, 1.06 mmol) at room temperature. The reaction mixture was refluxed for 2 hours and cooled to room temperature. After filtration through a Celite pad, the filtrate was concentrated in vacuo. The residue was purified by column chromatography on SiO₂ (Hexanes:EtOAc=1:1) to afford 1-(6-methylpyridin-2-yl)-2-(pyrazolo[1,5-a]pyridin-5-yl)ethane-1,2-dione (70 mg, 37%) as a yellow solid. ¹H-NMR (400 MHz, DMSO-d₆): δ 8.85 (1H, d, J=6.8 Hz), 8.31 (1H, s), 8.16 (1H, d, J=2.4 Hz), 8.05 (1H, s), 7.63 (1H, q, J=3.1 Hz), 6.78 (1H, dd, J=7.2, 1.6 Hz), 7.30 (1H, dd, J=7.2, 2.0 Hz), 6.95 (1H, d, J=2.0 Hz), 2.39 (3H, s).

Step D: 5-(2-(dimethyoxymethyl)-5-(6-methylpyridin-2-yl)-1H-imidazol-4-yl)pyrazolo[1,5-a]pyridine

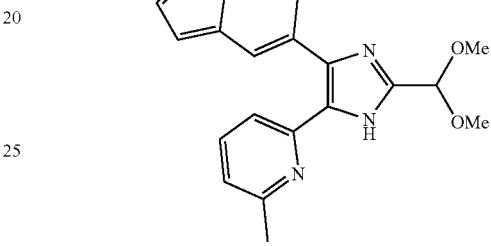

To a solution of 1-(6-methylpyridin-2-yl)-2-(pyrazolo[1,5-a]pyridin-5-yl)ethane-1,2-dione (70 mg, 0.264 mmol) in MTBE (1.8 mL) was added 2,2-dimethoxyacetaldehyde (0.080 mL, 0.528 mmol) followed by a solution of ammonium acetate (61 mg, 0.792 mmol) in MeOH (0.90 mL) at room temperature. The reaction mixture was stirred at room temperature for 1 hour and then concentrated in vacuo. The residue was partitioned between CHCl₃ and saturated aq. NaHCO₃. The separated aqueous layer was extracted with CHCl₃ twice. The combined organic layers were dried over Na₂SO₄, filtered and concentrated in vacuo. The residue was purified by column chromatography on SiO₂ (EtOAc only) to afford 5-(2-(dimethyoxymethyl)-5-(6-methylpyridin-2-yl)-1H-imidazol-4-yl)pyrazolo[1,5-a]pyridine (77 mg, 84%) as a pale yellow solid. ¹H-NMR (400 MHz, CDCl₃): δ 10.4 (1H, s), 8.46 (1H, d, J=6.8 Hz), 7.96 (1H, d, J=2.4 Hz), 7.89 (1H, s), 7.46 (1H, t, J=7.6 Hz), 7.35 (1H, d, J=8.0 Hz), 7.05-7.01 (2H, m), 6.51 (1H, d, J=2.0 Hz), 5.57 (1H, s), 3.48 (6H, s), 2.59 (3H, s).

Step E: 5-(6-emthylpyridin-2-yl)-4-(pyrazolo[1,5-a]pyridin-5-yl)-1H-imidazole-2-carbaldehyde

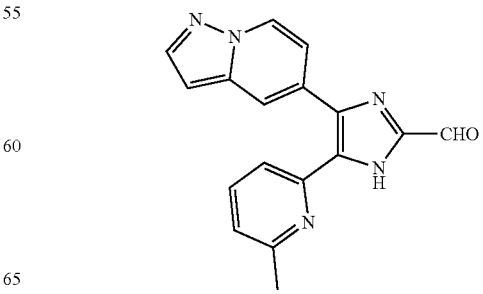

A mixture of 5-(2-(dimethyoxymethyl)-5-(6-methylpyridin-2-yl)-1H-imidazol-4-yl)pyrazolo[1,5-a]pyridine (77 mg, 0.222 mmol) and 1 N aq. HCl (2.2 mL, 2.2 mmol) was stirred at 70° C. for 4 hours and cooled to 0° C. The reaction mixture was neutralized with saturated aq. NaHCO₃ at 0° C. and extracted with a mixture of CHCl₃ and MeOH (v/v=4/1) twice. The combined organic layers were dried over Na₂SO₄, filtered and concentrated in vacuo. The residual solid was suspended in diethyl ether collected by filtration, washed with diethyl ether, and dried under vacuum to afford 5-(6-emthylpyridin-2-yl)-4-(pyrazolo[1,5-a]pyridin-5-yl)-1H-imidazole-2-carbaldehyde (16 mg, 24%) as a yellow solid. ¹H-NMR (400 MHz, CDCl₃): δ 9.83 (1H, s), 8.54 (1H, d, J=7.2 Hz), 8.01 (1H, d, J=2.4 Hz), 7.90 (1H, s), 7.53 (1H, t, J=7.8 Hz), 7.43 (1H, d, J=7.6 Hz), 7.13 (1H, d, J=7.2 Hz), 7.04 (1H, dd, J=6.8, 1.6 Hz), 6.59 (1H, d, J=2.0 Hz), 2.62 (3H, s).

Intermediate 4

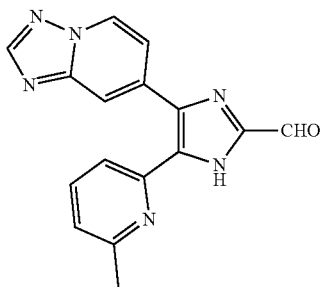 [SMILES: Cc1cccc(-c2[nH]c(C=O)nc2-c2ccn3ncnc3c2)n1]

Step A

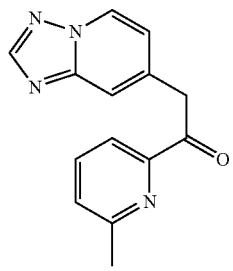 [SMILES: Cc1cccc(C(=O)Cc2ccn3ncnc3c2)n1]

A mixture of diphenyl (6-methylpyridin-2-yl)(phenylamino)methylphosphonate (527 mg, 1.22 mmol), [1,2,4]triazolo[1,5-a]pyridine-7-carbaldehyde (Intermediate 2, 180 mg, 1.22 mmol) and cesium carbonate (518 mg, 1.59 mmol) in a mixture of THF (8.0 mL) and i-PrOH (2.0 mL) was stirred at room temperature overnight. After addition of 2 N aq. HCl (6.0 mL), the reaction mixture of stirred at room temperature for an additional 1 hour and then neutralized with saturated aq. NaHCO₃ at 0° C. The mixture was extracted with DCM twice. The combined organic layers were dried over Na₂SO₄, filtered and concentrated in vacuo. The residue was purified by column chromatography on SiO₂ (Hexanes:EtOAc=1:2 to 1:4) to afford 2-([1,2,4]triazolo[1,5-a]pyridin-7-yl)-1-(6-methylpyridin-2-yl)ethanone (283 mg, 92%) as a yellow solid. ¹H-NMR (400 MHz, CDCl₃): δ 8.53 (1H, d, J=6.8 Hz), 8.30 (1H, s), 7.88 (1H, d, J=7.6 Hz), 7.75-7.71 (2H, m), 7.37 (1H, d, J=8.0 Hz), 7.06 (1H, dd, J=7.2, 1.6 Hz), 4.68 (2H, s), 2.68 (3H, s).

Step B: 1-([1,2,4]triazolo[1,5-a]pyridin-7-yl)-2-(6-methylpyridin-2-yl)ethane-1,2-dione

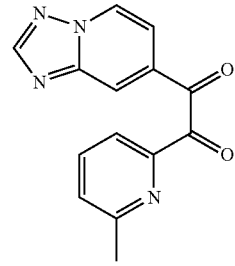 [SMILES: Cc1cccc(C(=O)C(=O)c2ccn3ncnc3c2)n1]

To a solution of 2-([1,2,4]triazolo[1,5-a]pyridin-7-yl)-1-(6-methylpyridin-2-yl)ethanone (220 mg, 0.793 mmol) in dioxane (7.9 mL) was added selenium dioxide (132 mg, 1.19 mmol) at room temperature. The reaction mixture was refluxed for 2 hours and cooled to room temperature. After filtration through a Celite pad, the filtrate was concentrated in vacuo. The residue was purified by column chromatography on SiO₂ (Hexanes:EtOAc=1:1) to afford 1-([1,2,4]triazolo[1,5-a]pyridine-7-yl)-2-(6-methylpyridin-2-yl)ethane-1,2-dione (130 mg, 56%) as a yellow solid. ¹H-NMR (400 MHz, CDCl₃): δ 8.75 (1H, d, J=6.8 Hz), 8.49 (1H, s), 8.18 (1H, s), 8.05 (1H, d, J=7.2 Hz), 7.85 (1H, t, J=7.8 Hz), 7.70 (1H, dd, J=7.0, 1.4 Hz), 7.42 (1H, d, J=8.0 Hz), 2.47 (3H, s).

Step C: 7-(2-(dimethoxymethyl)-5-(6-methylpyridin-2-yl)-1H-imidazol-4-yl)[1,2,4]triazolo[1,5a]pyridine

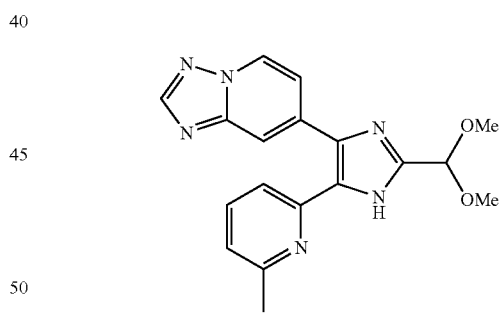

To a solution of 1-([1,2,4]triazolo[1,5-a]pyridin-7-yl)-2-(6-methylpyridin-2-yl)ethane-1,2-dione (160 mg, 0.601 mmol) in MTBE (4.0 mL) was added 2,2-dimethoxyacetaldehyde (0.180 mL, 1.20 mmol) followed by a solution of ammonium acetate (139 mg, 1.80 mmol) in MeOH (2.0 mL) at room temperature. The reaction mixture was stirred at room temperature for 1 hour, and then concentrated in vacuo. The residue was partitioned between CHCl₃ and saturated aq. NaHCO₃. The separated aqueous layer was extracted with CHCl₃ twice. The combined organic layers were dried over Na₂SO₄, filtered and concentrated in vacuo. The residue was purified by column chromatography on SiO₂ (DCM:MeOH=100:1) to afford 7-(2-(dimethoxymethyl)-5-(6-methylpyridin-2-yl)-1H-imidazol-4-yl)[1,2,4]triazolo[1,5a]pyridine (142 mg, 67%) as a yellow solid.

¹H-NMR (400 MHz, CDCl₃): δ 10.61 (1H, brs), 8.59 (1H, d, J=6.8 Hz), 8.35 (1H, s), 8.08 (1H, s), 7.51-7.46 (2H, m), 7.38 (1H, d, J=7.6 Hz), 7.07 (1H, d, J=8.0 Hz), 5.57 (1H, s), 3.47 (6H, s), 2.59 (3H, s).

Step D: 4-([1,2,4]triazolo[1,5-a]pyridin-7-yl)-5-(6-methylpyridin-2-yl)-1H-imidazole-2-carbaldehyde

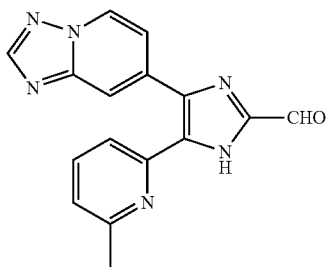 [SMILES: Cc1cccc(-c2[nH]c(C=O)nc2-c2ccn3ncnc3c2)n1]

A mixture of 7-(2-(dimethoxymethyl)-5-(6-methylpyridin-2-yl)-1H-imidazol-4-yl)-[1,2,4]triazolo[1,5a]pyridine (142 mg, 0.405 mmol) and 1 N aq. HCl (4.0 mL) was stirred at 70° C. for 4 hours and cooled to 0° C. After neutralized with saturated aq. NaHCO₃ at 0° C., the mixture was extracted with a mixture of CHCl₃ and MeOH (v/v=4/1) twice. The combined organic layers were dried over Na₂SO₄, filtered and concentrated in vacuo. The residual solid was suspended in diethyl ether collected by filtration, washed with diethyl ether, and dried under vacuum to afford 4-([1,2,4]triazolo[1,5-a]pyridin-7-yl)-5-(6-methylpyridin-2-yl)-1H-imidazole-2-carbaldehyde (86 mg, 70%) as a yellow solid. ¹H-NMR (400 MHz, DMSO-d₆): δ 9.80 (1H, s), 8.93 (1H, d, J=7.2 Hz), 8.52 (1H, s), 8.25 (1H, s), 7.81 (2H, t, J=7.6 Hz), 7.69 (1H, brs), 7.50 (1H, dd, J=7.4, 1.8 Hz), 7.30 (1H, brs), 2.50 (3H, s).

Example 1

3-chloro-2-fluoro-N-((5-(6-methylpyridin-2-yl)-4-(pyrazolo[1,5-a]pyridin-5-yl)-1H-imidazol-2-yl)methyl)aniline

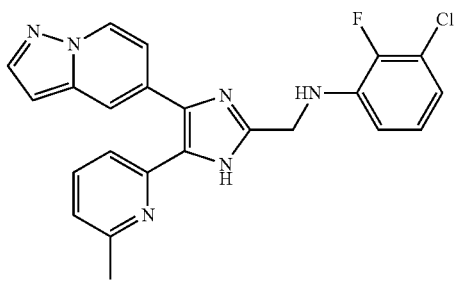 [SMILES: Cc1cccc(-c2[nH]c(CNc3cccc(Cl)c3F)nc2-c2ccn3nccc3c2)n1]

A mixture of 5-(6-emthylpyridin-2-yl)-4-(pyrazolo[1,5-a]pyridin-5-yl)-1H-imidazole-2-carbaldehyde (Intermediate 3, 16 mg, 0.0530 mmol), 3-chloro-2-fluoroaniline (0.0870 mL, 0.0790 mmol) and acetic acid (3.0 μL, 0.0530 mmol) in DCE (1.1 mL) was refluxed for 2 hours and cooled to 0° C. After addition of MeOH (1.1 mL), THF (0.3 mL) followed by NaBH₄ (8.0 mg, 0.211 mmol), the reaction mixture was allowed to warm to room temperature and stirred for an additional 1 hour. After quenched with saturated aq. NH₄Cl, the mixture was extracted with CHCl₃ twice. The combined organic layers were dried over Na₂SO₄, filtered and concentrated in vacuo. The residue was purified by column chromatography on NH—SiO₂ (EtOAc only) to afford 3-chloro-2-fluoro-N-((5-(6-methylpyridin-2-yl)-4-(pyrazolo[1,5-a]pyridin-5-yl)-1H-imidazol-2-yl)methyl)aniline (6.4 mg, 28%) as a yellow solid. ¹H-NMR (400 MHz, CD₃OD): δ 8.46 (1H, d, J=7.2 Hz), 7.94 (1H, d, J=2.0 Hz), 7.82 (1H, s), 7.66 (1H, t, J=8.0 Hz), 7.34 (1H, d, J=8.0 Hz), 7.20 (1H, d, J=7.2 Hz), 6.94-6.89 (2H, m), 6.74 (1H, t, J=8.0 Hz), 6.68 (1H, t, J=7.2 Hz), 6.59 (1H, d, J=2.0 Hz), 4.55 (2H, s), 2.52 (3H, s). MS: 433.1 (M+H⁺).

Example 2

3,4-dichloro-N-((5-(6-methylpyridin-2-yl)-4-(pyrazolo[1,5-a]pyridin-5-yl)-1H-imidazol-2-yl)methyl)aniline

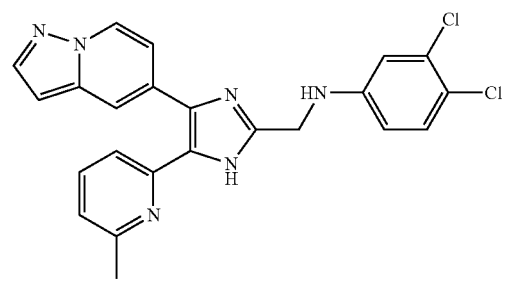

5-(6-emthylpyridin-2-yl)-4-(pyrazolo[1,5-a]pyridin-5-yl)-1H-imidazole-2-carbaldehyde (Intermediate 3, 70 mg, 0.231 mmol) was reacted with 3,4-dichloroaniline (56 mg, 0.346 mmol) under the conditions of Example 1. The crude product was purified by column chromatography on NH—SiO₂ (EtOAc:MeOH=100:1) to afford 3,4-dichloro-N-((5-(6-methylpyridin-2-yl)-4-(pyrazolo[1,5-a]pyridin-5-yl)-1H-imidazol-2-yl)methyl)aniline (24 mg, 24%) as an ivory solid. ¹H-NMR (400 MHz, CD₃OD): δ 8.46 (1H, s), 7.94 (1H, d, J=2.4 Hz), 7.84 (1H, s), 7.64 (1H, s), 7.28 (1H, s), 7.21-7.19 (2H, m), 6.98 (1H, s), 6.85 (1H, d, J=2.4 Hz), 6.64 (1H, dd, J=8.8, 2.8 Hz), 6.59 (1H, d, J=2.0 Hz), 4.45 (2H, s), 2.53 (3H, s). MS: 449.1 (M+H⁺)

Example 3

N-((4-([1,2,4]triazolo[1,5-a]pyridin-7-yl)-5-(6-methylpyridin-2-yl)-1H-imidazol-2-yl)methyl)-2-fluoroaniline

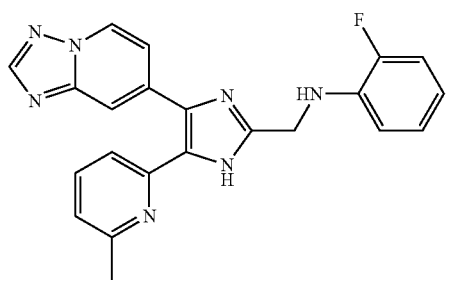 [SMILES: Cc1cccc(-c2[nH]c(CNc3ccccc3F)nc2-c2ccn3ncnc3c2)n1]

4-([1,2,4]triazolo[1,5-a]pyridin-7-yl)-5-(6-methylpyridin-2-yl)-1H-imidazole-2-carbaldehyde (Intermediate 4, 37 mg, 0.122 mmol) was reacted with 2-fluoroaniline (18 μL, 0.182 mmol) under the conditions of Example 1. The crude product was purified by column chromatography on SiO$_2$ (DCM:MeOH=95:5) to afford N-((4-([1,2,4]triazolo[1,5-a]pyridin-7-yl)-5-(6-methylpyridin-2-yl)-1H-imidazol-2-yl)methyl)-2-fluoroaniline (34 mg, 70%) as a yellow solid. $^1$H-NMR (400 MHz, CDCl$_3$): δ 10.70 (1H, brs), 8.60 (1H, d, J=6.8 Hz), 8.36 (1H, s), 8.09 (1H, s), 7.52-7.45 (2H, m), 7.36 (1H, d, J=8.0 Hz), 7.07-6.98 (3H, m), 6.79-6.69 (2H, m), 4.60-4.57 (3H, m), 2.48 (3H, s). MS: 400.2 (M+H$^+$).

Example 4

N-((4-([1,2,4]triazolo[1,5-a]pyridin-7-yl)-5-(6-methylpyridin-2-yl)-1H-imidazol-2-yl)methyl)-3-chloro-2-fluoroaniline

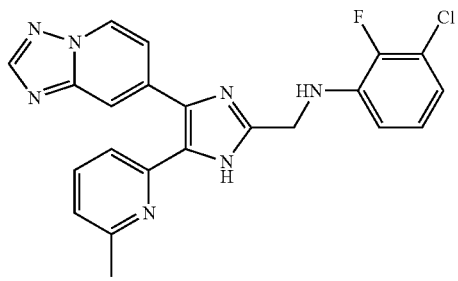 [SMILES: Cc1cccc(-c2[nH]c(CNc3cccc(Cl)c3F)nc2-c2ccn3ncnc3c2)n1]

4-([1,2,4]triazolo[1,5-a]pyridin-7-yl)-5-(6-methylpyridin-2-yl)-1H-imidazole-2-carbaldehyde (Intermediate 4, 42 mg, 0.138 mmol) was reacted with 3-chloro-2-fluoroaniline (23 μL, 0.207 mmol) under the conditions of Example 1. The crude product was purified by column chromatography on NH—SiO$_2$ (EtOAc only) to afford N-((4-([1,2,4]triazolo[1,5-a]pyridin-7-yl)-5-(6-methylpyridin-2-yl)-1H-imidazol-2-yl)methyl)-3-chloro-2-fluoroaniline (16 mg, 27%) as a white solid. $^1$H-NMR (400 MHz, CD$_3$OD): δ 8.71 (1H, d, J=7.2 Hz), 8.34 (1H, s), 7.96 (1H, s), 7.70 (1H, s), 7.40-7.34 (2H, m), 7.24 (1H, d, J=7.6 Hz), 6.92 (1H, td, J=8.2, 1.3 Hz), 6.74 (1H, t, J=8.0 Hz), 6.69 (1H, td, J=7.3, 1.3 Hz), 4.56 (2H, s), 2.53 (3H, s). MS: 434.1 (M+H$^+$).

Example 5

N-((4-([1,2,4]triazolo[1,5-a]pyridin-7-yl)-5-(6-methylpyridin-2-yl)-1H-imidazol-2-yl)methyl)-3,4-dichloroaniline

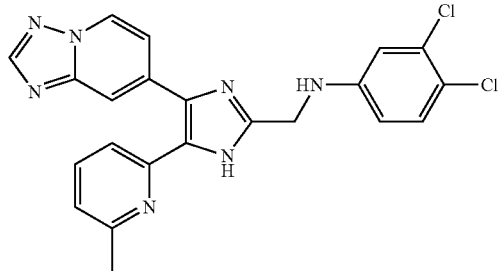 [SMILES: Cc1cccc(-c2[nH]c(CNc3ccc(Cl)c(Cl)c3)nc2-c2ccn3ncnc3c2)n1]

4-([1,2,4]triazolo[1,5-a]pyridin-7-yl)-5-(6-methylpyridin-2-yl)-1H-imidazole-2-carbaldehyde (Intermediate 4, 42 mg, 0.138 mmol) was reacted with 3,4-dichloroaniline (34 mg, 0.207 mmol) under the conditions of Example 1. The crude product was purified by column chromatography on NH—SiO$_2$ (EtOAc:MeOH=100:1) to afford N-((4-([1,2,4]triazolo[1,5-a]pyridin-7-yl)-5-(6-methylpyridin-2-yl)-1H-imidazol-2-yl)methyl)-3,4-dichloroaniline (22 mg, 35%) as a white solid. $^1$H-NMR (400 MHz, CD$_3$OD): δ 8.71 (1H, d, J=7.2 Hz), 8.38 (1H, s), 7.96 (1H, s), 7.71 (1H, t, J=8.0 Hz), 7.38 (2H, s), 7.24 (1H, d, J=7.6 Hz), 7.20 (1H, d, J=8.8 Hz), 6.86 (1H, d, J=2.8 Hz), 6.64 (1H, dd, J=8.8, 2.8 Hz), 4.46 (2H, s), 2.52 (3H, s). MS: 450.1 (M+H$^+$).

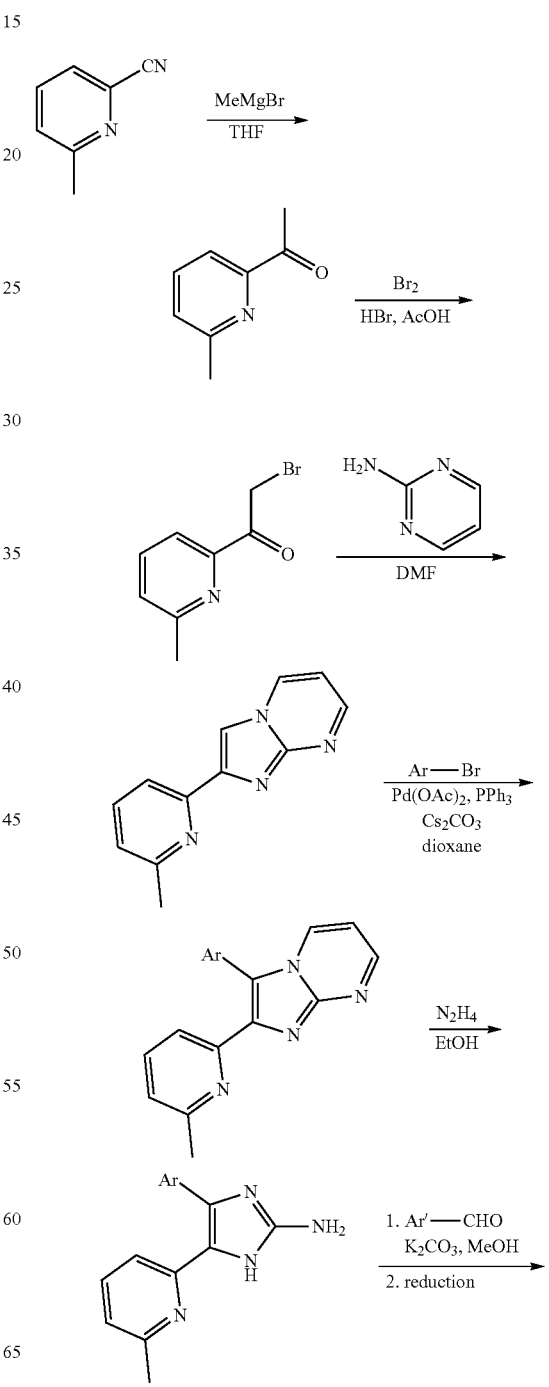

-continued

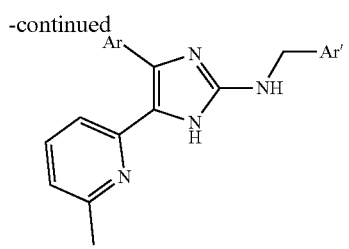

Intermediate 5

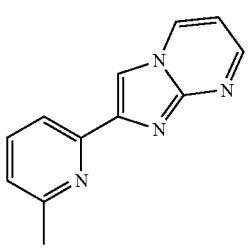 [SMILES: Cc1cccc(-c2cn3cccnc3n2)n1]

Step A: 1-(6-methylpyridin-2-yl)ethanone

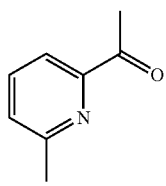

To a solution of 6-methylpicolinonitrile (4.50 g, 38.1 mmol) in dry THF (127 mL) was slowly added methylmagnesium bromide (3.0 M solution in THF, 38.1 mL, 114 mmol) at −20° C. The reaction mixture was stirred at −20° C. for 5 hours and quenched with saturated aq. NH₄Cl. The mixture was stirred at room temperature overnight and extracted with EtOAc twice. The combined organic layers were washed with water and brine, dried over Na₂SO₄, filtered and concentrated in vacuo. The residue was purified by column chromatography on SiO₂ (Hexanes:EtOAc=5:1) to give 1-(6-methylpyridin-2-yl)ethanone (3.70 g, 72%) as a colorless oil. ¹H-NMR (400 MHz, CDCl₃): δ 7.62 (1H, d, J=7.6 Hz), 7.49 (1H, t, J=7.6 Hz), 7.12 (1H, d, J=7.2 Hz), 2.51 (3H, s), 2.41 (3H, s).

Step B: 2-bromo-1-(6-methylpyridin-2-yl)ethanone

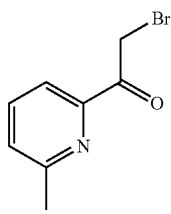

To a solution of 1-(6-methylpyridin-2-yl)ethanone (3.70 g, 27.4 mmol) and HBr (33% solution in AcOH, 9.01 mL, 54.7 mmol) was slowly added Br₂ (1.55 mL, 30.1 mmol) at 0° C. The reaction mixture was stirred at room temperature for 1 hour and then treated with water. The mixture was extracted with EtOAc twice. The combined organic layers were washed with water and brine, dried over Na₂SO₄, filtered and concentrated in vacuo. The residue was purified by column chromatography on SiO₂ (Hexanes:EtOAc=10:1) to give 2-bromo-1-(6-methylpyridin-2-yl)ethanone (4.40 g, 75%) as a colorless oil. ¹H-NMR (400 MHz, CDCl₃): δ 7.84 (1H, d, J=8.0 Hz), 7.69 (1H, t, J=7.6 Hz), 7.32 (1H, d, J=7.2 Hz), 4.85 (2H, s), 2.56 (3H, s).

Step C: 2-(6-methylpyridin-2-yl)imidazo[1,2-a]pyrimidine

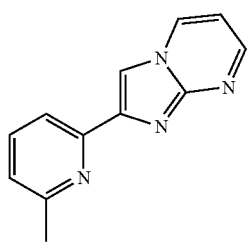 [SMILES: Cc1cccc(-c2cn3cccnc3n2)n1]

To a solution of 2-bromo-1-(6-methylpyridin-2-yl)ethanone (4.40 g, 20.6 mmol) in DMF (69 mL) was added pyrimidin-2-amine (5.86 g, 61.7 mmol) at room temperature. The reaction mixture was heated at 80° C. for 2 hours. After concentration in vacuo, the residue was treated with DCM. A precipitated solid was collected by filtration, washed with DCM and dried under vacuum to afford 2-(6-methylpyridin-2-yl)imidazo[1,2-a]pyrimidine (2.96 g, 69%) as a pale yellow solid. ¹H-NMR (400 MHz, CD₃OD): δ 8.92 (1H, dd, J=6.8, 2.0 Hz), 8.60 (1H, dd, J=3.6, 2.0 Hz), 8.39 (1H, s), 7.96 (1H, d, J=8.0 Hz), 7.80 (1H, t, J=7.8 Hz), 7.25 (1H, d, J=7.6 Hz), 7.08 (1H, dd, J=6.7, 3.7 Hz), 2.59 (3H, s).

Intermediate 6

5-(6-methylpyridin-2-yl)4-(pyrazolo[1,5-a]pyridine-5yl)-1H-imdazol-2-amine

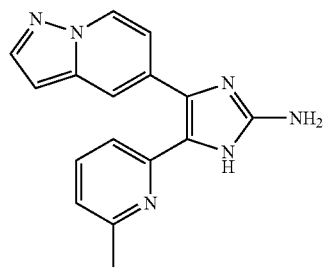 [SMILES: Cc1cccc(-c2[nH]c(N)nc2-c2ccn3nccc3c2)n1]

Step A: 2-(6-methylpyridin-2-yl)-3-(pyrazolo[1,5-a]pyridine-5-yl)imidazo[1,2-a]pyrimidine

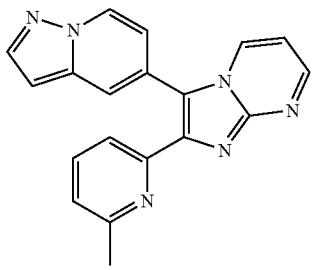 [SMILES: Cc1cccc(-c2nc3ncccn3c2-c2ccn3nccc3c2)n1]

A mixture of 2-(6-methylpyridin-2-yl)imidazo[1,2-a]pyrimidine (Intermediate 5, 300 mg, 1.43 mmol), 5-bromopyrazolo[1,5-a]pyridine (281 mg, 1.43 mmol), Pd(OAc)$_2$ (26.0 mg, 0.114 mmol), PPh$_3$ (60 mg, 0.228 mmol) and Cs$_2$CO$_3$ (511 mg, 1.57 mmol) in dioxane (4.8 mL) was degassed by purging and re-filled with Ar in several times. The reaction mixture was stirred at 120° C. overnight. After cooled to room temperature, the reaction mixture was diluted with EtOAc and washed with water and brine. The separated organic layer was dried over Na$_2$SO$_4$, filtered and concentrated in vacuo. The residue was purified by column chromatography on NH—SiO$_2$ (EtOAc only to EtOAc:MeOH=100:1) to afford 2-(6-methylpyridin-2-yl)-3-(pyrazolo[1,5-a]pyridine-5-yl)imidazo[1,2-a]pyrimidine (178 mg, 38%) as a yellow solid. $^1$H-NMR (400 MHz, CDCl$_3$): δ 8.63 (1H, q, J=2.0 Hz), 8.58 (1H, d, J=7.2 Hz), 8.46 (1H, dd, J=6.8, 2.0 Hz), 8.07-8.04 (2H, m), 7.83 (1H, s), 7.65 (1H, t, J=7.8 Hz), 7.06 (1H, d, J=8.0 Hz), 6.93-6.89 (2H, m), 6.63 (1H, d, J=2.4 Hz), 2.33 (3H, s).

Step B: 5-(6-methylpyridin-2-yl)4-(pyrazolo[1,5-a]pyridine-5yl)-1H-imdazol-2-amine

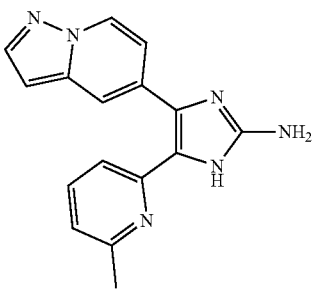 [SMILES: Cc1cccc(-c2[nH]c(N)nc2-c2ccn3nccc3c2)n1]

A mixture of 2-(6-methylpyridin-2-yl)-3-(pyrazolo[1,5-a]pyridine-5-yl)imidazo[1,2-a]pyrimidine (178 mg, 0.545 mmol) and 20% hydrazine (1.1 mL) in EtOH (5.5 mL) was refluxed for 1 hour. After concentration in vacuo, the residue was treated with DCM. A precipitated solid was collected by filtration and dried under vacuum to afford 5-(6-methylpyridin-2-yl)4-(pyrazolo[1,5-a]pyridine-5yl)-1H-imdazol-2-amine (108 mg, 68%) as a yellow solid. $^1$H-NMR (400 MHz, CD$_3$OD): δ 8.42 (1H, d, J=6.8 Hz), 7.92 (1H, d, J=2.4 Hz), 7.78 (1H, s), 7.56 (1H, t, J=7.8 Hz), 7.27 (1H, d, J=8.0 Hz), 7.08 (1H, d, J=7.6 Hz), 6.95 (1H, d, J=7.6 Hz), 6.55 (1H, d, J=2.0 Hz), 2.50 (3H, s).

Intermediate 7

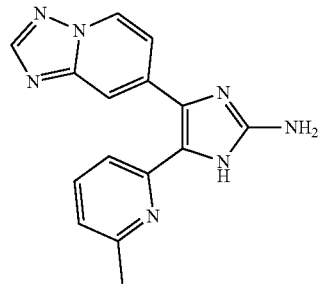 [SMILES: Cc1cccc(-c2[nH]c(N)nc2-c2ccn3ncnc3c2)n1]

Step A: (E)-N-(4-bromopyridin-2-yl)-N'-hydroxyformimidamide

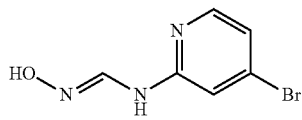 [SMILES: O/N=C/Nc1cc(Br)ccn1]

To a solution of 4-bromopyridin-2-amine (10 g, 57.8 mmol) in IPA (193 mL) was added 1,1-dimethoxy-N,N-dimethylmethanamine (9.98 mL, 75.0 mmol) at room temperature. The mixture was refluxed for 3 hours, and cooled to 50° C. After addition of hydroxylamine hydrochloride (5.22 g, 75.0 mmol), the reaction mixture was stirred at 50° C. overnight, and cooled to room temperature. A precipitated solid was collected by filtration, washed with DCM and dried under vacuum to afford (E)-N-(4-bromopyridin-2-yl)-N'-hydroxyformimidamide (11.2 g, 90%) as a white solid. $^1$H-NMR (400 MHz, CD$_3$OD): δ 8.01 (1H, d, J=5.6 Hz), 7.90 (1H, s), 7.17 (1H, d, J=1.2 Hz), 7.06 (1H, dd, J=5.6, 1.6 Hz).

Step B: 7-bromo-[1,2,4]triazolo[1,5-a]pyridine

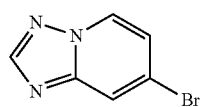

To a solution (E)-N-(4-bromopyridin-2-yl)-N'-hydroxyformimidamide (11.2 g, 51.8 mmol) in dry THF (173 mL) was added TFAA (8.05 mL, 57.0 mmol) at 0° C. After heated at 50° C. for 2 hours, the reaction mixture was neutralized with saturated aq. NaHCO$_3$ and extracted with DCM twice. The combined organic layers were washed with brine, dried over Na$_2$SO$_4$, filtered and concentrated in vacuo. The residue was purified by column chromatography on SiO$_2$ (Hexanes:EtOAc=1:1) to give 7-bromo-[1,2,4]triazolo[1,5-a]pyridine (8.49 g, 83%) as a white solid. $^1$H-NMR (400 MHz, CDCl$_3$): δ 8.47 (1H, d, J=7.6 Hz), 8.33 (1H, s), 7.98 (1H, d, J=2.0 Hz), 7.16 (1H, dd, J=7.4, 1.8 Hz).

Step C: 7-(2-(6-methylpyridin-2-yl)imidazo[1,2-a]pyrimidin-3-yl)-[1,2,4]triazolo[1,5-a]pyridine

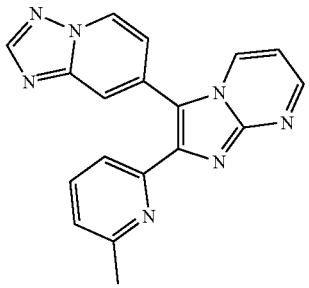 [SMILES: Cc1cccc(-c2nc3ncccn3c2-c2ccn3ncnc3c2)n1]

A mixture of 2-(6-methylpyridin-2-yl)imidazo[1,2-a]pyrimidine (Intermediate 5, 4.45 g, 21.2 mmol), 7-bromo-[1,2,4]triazolo[1,5-a]pyridine (6.29 g, 31.8 mmol), Pd(OAc)$_2$ (380 mg, 1.69 mmol), PPh$_3$ (888 mg, 3.39 mmol) and Cs$_2$CO$_3$ (7.59 g, 23.4 mmol) in dioxane (71 mL) was degassed by purging and re-filled with Ar in several times. The reaction mixture was stirred at 120° C. overnight. After cooled to room temperature, the reaction mixture was partitioned between EtOAc and water. The separated organic layer was washed with brine, dried over Na$_2$SO$_4$, filtered and concentrated in vacuo. The residue was purified by column chromatography on NH—SiO$_2$ (EtOAc only) to afford 7-(2-(6-methylpyridin-2-yl)imidazo[1,2-a]pyrimidin-3-yl)-[1,2,4]triazolo[1,5-a]pyridine (3.63 g, 52%) as a pale yellow solid. $^1$H-NMR (400 MHz, CDCl$_3$): δ 8.69 (1H, d, J=7.2 Hz), 8.66 (1H, dd, J=4.2, 1.8 Hz), 8.48 (1H, dd, J=6.6, 1.8 Hz), 8.45 (1H, s), 8.14 (1H, d, J=8.0 Hz), 8.02 (1H, s), 7.68 (1H, t, J=7.6 Hz), 7.31 (1H, dd, J=7.0, 1.4 Hz), 7.07 (1H, d, J=7.6 Hz), 6.94 (1H, dd, J=6.8, 4.0 Hz), 2.29 (3H, s).

Step D: 4-([1,2,4]triazolo[1,5-a]pyridin-7-yl)-5-(6-methylpyridin-2-yl)-1H-imidazol-2-amine

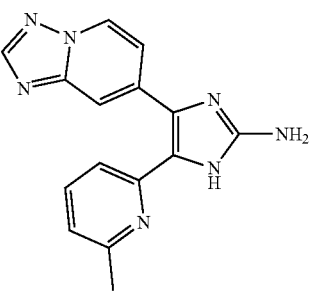 [SMILES: Cc1cccc(-c2[nH]c(N)nc2-c2ccn3ncnc3c2)n1]

A mixture of 7-(2-(6-methylpyridin-2-yl)imidazo[1,2-a]pyrimidin-3-yl)-[1,2,4]triazolo[1,5-a]pyridine (3.63 g, 11.1 mmol) and 20% hydrazine (2.2 mL) in EtOH (111 mL) was refluxed for 1 hour and then concentrated in vacuo. The residue was purified by column chromatography on NH—SiO$_2$ (DCM:MeOH=20:1) to afford 4-([1,2,4]triazolo[1,5-a]pyridin-7-yl)-5-(6-methylpyridin-2-yl)-1H-imidazol-2-amine (2.30 g, 71%) as a yellow solid. $^1$H-NMR (400 MHz, CD$_3$OD): δ 8.65 (1H, d, J=7.2 Hz), 8.35 (1H, s), 7.91 (1H, s), 7.63 (1H, t, J=8.0 Hz), 7.33 (2H, d, J=7.2 Hz), 7.15 (1H, d, J=7.6 Hz), 2.51 (3H, s).

Example 6

N-(2-fluorobenzyl)-5-(6-methylpyridin-2-yl)-4-(pyrazolo[1,5-a]pyridine-5-yl)-1H-imidazol-2-amine

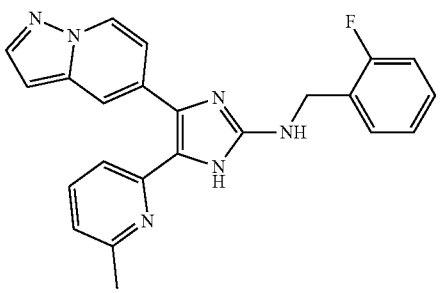 [SMILES: Cc1cccc(-c2[nH]c(NCc3ccccc3F)nc2-c2ccn3nccc3c2)n1]

A mixture of 5-(6-methylpyridin-2-yl)4-(pyrazolo[1,5-a]pyridine-5yl)-1H-imdazol-2-amine (Intermediate 6, 54 mg, 0.186 mmol), 2-fluorobenzaldehyde (0.0300 mL, 0.242 mmol) and K$_2$CO$_3$ (51.0 mg, 0.372 mmol) in MeOH (1.9 mL) was stirred at room temperature for 18 hours. After filtered through a Celite pad, the residue was concentrated in vacuo. The residue was dissolved in MeOH (1.9 mL). After addition of Pd/C (10 wt %, 20.0 mg, 0.0190 mmol), the reaction mixture was stirred at room temperature for 4 hours under H$_2$ atmosphere (balloon). After filtration through a Celite pad, the filtrate was concentrated in vacuo. The residue was diluted with DCM and washed with water and brine. The separated organic layer was dried over Na$_2$SO$_4$, filtered and concentrated in vacuo. The residue was purified by column chromatography on NH—SiO$_2$ (DCM:MeOH=200:1) to afford N-(2-fluorobenzyl)-5-(6-methylpyridin-2-yl)-4-(pyrazolo[1,5-a]pyridine-5-yl)-1H-imidazol-2-amine (3.0 mg, 4%) as a yellow solid. $^1$H-NMR (400 MHz, CD$_3$OD): δ 8.42 (1H, d, J=7.2 Hz), 7.92 (1H, d, J=2.0 Hz), 7.78 (1H, s), 7.56 (1H, t, J=7.6 Hz), 7.50 (1H, t, J=7.2 Hz), 7.30-7.25 (2H, m), 7.15 (1H, t, J=7.6 Hz), 7.12-7.08 (2H, m), 6.92 (1H, d, J=6.8 Hz), 6.55 (1H, d, J=1.6 Hz), 4.62 (2H, s), 2.50 (3H, s). MS: 398.44 (M+H$^+$).

Example 7

N-(3-fluorobenzyl)-5-(6-methylpyridin-2-yl)-4-(pyrazolo[1,5-a]pyridine-5-yl)-1H-imidazol-2-amine

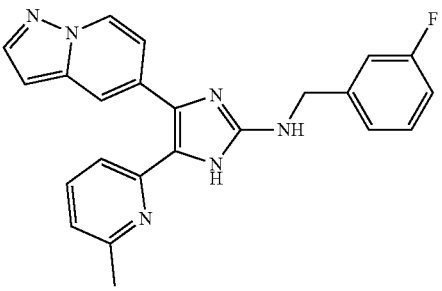 [SMILES: Cc1cccc(-c2[nH]c(NCc3cccc(F)c3)nc2-c2ccn3nccc3c2)n1]

5-(6-methylpyridin-2-yl)4-(pyrazolo[1,5-a]pyridine-5yl)-1H-imdazol-2-amine (1) (Intermediate 6, 250 mg, 0.861 mmol) was reacted with 3-fluorobenzaldehyde (0.119 mL, 1.12 mmol) under the conditions of Example 6. The crude product was purified by prep HPLC (C18 column) to afford N-(3-fluorobenzyl)-5-(6-methylpyridin-2-yl)-4-(pyrazolo[1,5-a]pyridine-5-yl)-1H-imidazol-2-amine (30 mg, 9%) as a yellow solid. $^1$H-NMR (400 MHz, CD$_3$OD): δ 8.42 (1H, d, J=6.7 Hz), 7.92 (1H, d, J=2.4 Hz), 7.78 (1H, s), 7.57 (1H, t, J=8.0 Hz), 7.35 (1H, q, J=7.2 Hz), 7.28-7.22 (2H, m), 7.17 (1H, d, J=10.4 Hz), 7.09 (1H, d, J=7.6 Hz), 6.98 (1H, t, J=8.4 Hz), 6.92 (1H, d, J=7.2 Hz), 6.55 (1H, d, J=1.6 Hz), 4.57 (2H, s), 2.50 (3H, s). MS: 399.2 (M+H$^+$).

Example 8

N-(3-chloro-2-fluorobenzyl)-5-(6-methylpyridin-2-yl)-4-(pyrazolo[1,5-a]pyridin-5-yl)-1H-imidazol-2-amine

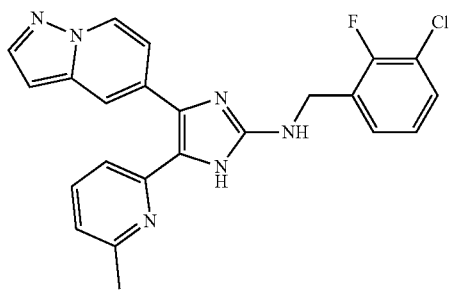 [SMILES: Cc1cccc(-c2[nH]c(NCc3cccc(Cl)c3F)nc2-c2ccn3nccc3c2)n1]

A mixture of 5-(6-methylpyridin-2-yl)-4-(pyrazolo[1,5-a]pyridin-5-yl)-1H-imidazol-2-amine (Intermediate 6, 150 mg, 0.517 mmol), 3-chloro-2-fluorobenzaldehyde (82.0 mg, 0.517 mmol) and K$_2$CO$_3$ (143 mg, 1.03 mmol) in MeOH (5.0 mL) was stirred at room temperature for 18 hours. After concentration, the residue was dissolved in THF (5.0 mL). After addition of borane-THF complex (1 M THF solution, 2.58 mL, 2.58 mmol) at room temperature, the reaction mixture was refluxed for 6 hours, cooled to room temperature and quenched with water. The mixture was extracted with DCM twice. The combined organic layers were washed with water and brine, dried over Na$_2$SO$_4$, filtered and concentrated in vacuo. The residue was purified by column chromatography on NH—SiO$_2$ (EtOAc only) to afford N-(3-chloro-2-fluorobenzyl)-5-(6-methylpyridin-2-yl)-4-(pyrazolo[1,5-a]pyridin-5-yl)-1H-imidazol-2-amine (71 mg, 32%) as a yellow solid. $^1$H-NMR (400 MHz, CD$_3$OD): δ 8.41 (1H, d, J=7.2 Hz), 7.91 (1H, d, J=2.0 Hz), 7.77 (1H, s), 7.56 (1H, t, J=7.8 Hz), 7.43 (1H, t, J=7.0 Hz), 7.37 (1H, t, J=6.8 Hz), 7.25 (1H, d, J=7.6 Hz), 7.13 (1H, t, J=7.8 Hz), 7.09 (1H, d, J=8.0 Hz), 6.92 (1H, d, J=6.8 Hz), 6.55 (1H, d, J=2.0 Hz), 4.64 (2H, s), 2.49 (3H, s). MS: 433.1 (M+H$^+$).

Example 9

N-(4-chloro-2-fluorobenzyl)-5-(6-methylpyridin-2-yl)-4-(pyrazolo[1,5-a]pyridin-5-yl)-1H-imidazol-2-amine

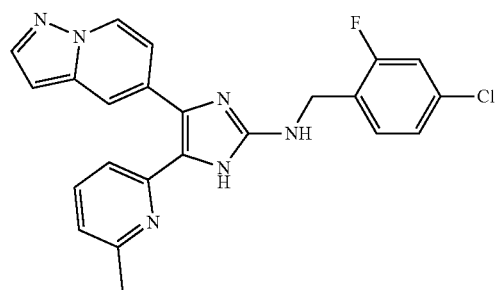 [SMILES: Cc1cccc(-c2[nH]c(NCc3ccc(Cl)cc3F)nc2-c2ccn3nccc3c2)n1]

A mixture of 5-(6-methylpyridin-2-yl)-4-(pyrazolo[1,5-a]pyridin-5-yl)-1H-imidazol-2-amine (Intermediate 6, 54 mg, 0.186 mmol), 4-chloro-2-fluorobenzaldehyde (38 mg, 0.242 mmol) and K$_2$CO$_3$ (51 mg, 0.372 mmol) in MeOH (1.9 mL) was stirred at room temperature for 18 hours. After filtered through a Celite pad, NaBH$_4$ (21 mg, 0.558 mmol) was added to the filtrate. The reaction mixture was refluxed for 3 hours and then concentrated in vacuo. The residue was diluted with saturated aq. NH$_4$Cl and extracted with DCM twice. The combined organic layers were washed with water and brine, dried over Na$_2$SO$_4$, filtered and concentrated in vacuo. The residue was purified by column chromatography on NH—SiO$_2$ (EtOAc only) to afford N-(4-chloro-2-fluorobenzyl)-5-(6-methylpyridin-2-yl)-4-(pyrazolo[1,5-a]pyridin-5-yl)-1H-imidazol-2-amine (24 mg, 30%) as a yellow solid. $^1$H-NMR (400 MHz, CDCl$_3$): δ 8.45 (1H, d, J=7.2 Hz), 7.95 (1H, d, J=2.0 Hz), 7.83 (1H, s), 7.44 (1H, t, J=7.0 Hz), 7.39 (1H, t, J=8.4 Hz), 7.30 (1H, d, J=8.4 Hz), 7.14-7.09 (2H, m), 7.01 (1H, dd, J=7.4, 1.8 Hz), 6.90 (1H, d, J=6.8 Hz), 6.50 (1H, d, J=2.4 Hz), 4.68 (1H, t, J=7.0 Hz), 4.58 (2H, d, J=6.0 Hz), 2.50 (3H, s). MS: 433.0 (M+H$^+$).

Example 10

N-(3,4-dichlorobenzyl)-5-(6-methylpyridin-2-yl)-4-(pyrazolo[1,5-a]pyridin-5-yl)-1H-imidazol-2-amine

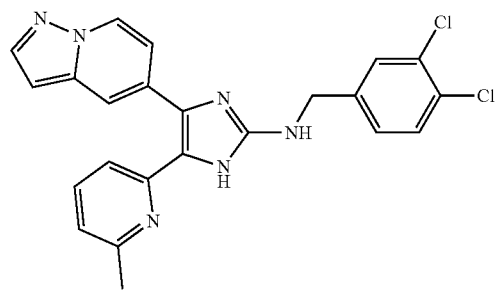 [SMILES: Cc1cccc(-c2[nH]c(NCc3ccc(Cl)c(Cl)c3)nc2-c2ccn3nccc3c2)n1]

A mixture of 5-(6-methylpyridin-2-yl)-4-(pyrazolo[1,5-a]pyridin-5-yl)-1H-imidazol-2-amine (Intermediate 6, 100 mg, 0.344 mmol), 3,4-dichlorobenzaldehyde (60 mg, 0.344 mmol) and K$_2$CO$_3$ (95 mg, 0.689 mmol) in MeOH (3.4 mL) was stirred at room temperature for 18 hours. After addition of LiBH₄ (15 mg, 0.689 mmol), the reaction mixture was stirred at room temperature for 3 hours. After concentration in vacuo, the residue was diluted with saturated aq. NH₄Cl and extracted with DCM twice. The combined organic layers were washed with water and brine, dried over Na₂SO₄, filtered and concentrated in vacuo. The residue was purified by column chromatography on NH—SiO₂ (EtOAc only) to afford N-(3,4-dichlorobenzyl)-5-(6-methylpyridin-2-yl)-4-(pyrazolo[1,5-a]pyridin-5-yl)-1H-imidazol-2-amine (47 mg, 30%) as a yellow solid. ¹H-NMR (400 MHz, CD₃OD): δ 8.42 (1H, d, J=7.2 Hz), 7.92 (1H, d, J=2.4 Hz), 7.77 (1H, s), 7.59-7.55 (2H, m), 7.48 (1H, d, J=8.4 Hz), 7.35 (1H, dd, J=8.6, 1.8 Hz), 7.26 (1H, s), 7.10 (1H, d, J=8.0 Hz), 6.91 (1H, d, J=6.0 Hz), 6.55 (1H, d, J=2.0 Hz), 4.53 (2H, s), 2.50 (3H, s). MS: 449.0 (M+H⁺).

Example 11

4-([1,2,4]triazolo[1,5-a]pyridin-7-yl)-N-(2-fluorobenzyl)-5-(6-methylpyridin-2-yl)-1H-imidazol-2-amine

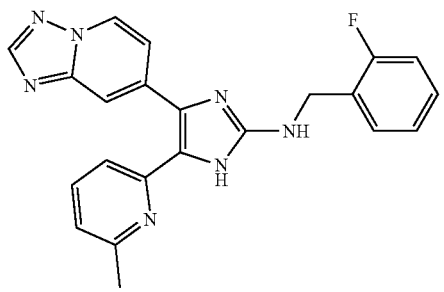 [SMILES: Cc1cccc(-c2[nH]c(NCc3ccccc3F)nc2-c2ccn3ncnc3c2)n1]

A mixture of 4-([1,2,4]triazolo[1,5-a]pyridin-7-yl)-5-(6-methylpyridin-2-yl)-1H-imidazol-2-amine (Intermediate 7, 100 mg, 0.343 mmol), 2-fluorobenzaldehyde (55 mg, 0.446 mmol), and K₂CO₃ (95 mg, 0.687 mmol) in MeOH (3.4 mL) was stirred at room temperature for 18 hours. After filtration through a Celite pad, NaBH 4 (39 mg, 1.03 mmol) was added to the filtrate at room temperature. The reaction mixture was refluxed for 3 hours and then concentrated in vacuo. The residue was diluted with saturated aq. NH₄Cl and extracted with DCM twice. The combined organic layers were washed with water and brine, dried over Na₂SO₄, filtered and concentrated in vacuo. The residue was purified by column chromatography on NH—SiO₂ (DCM only to DCM:MeOH=100:1) to afford 4-([1,2,4]triazolo[1,5-a]pyridin-7-yl)-N-(2-fluorobenzyl)-5-(6-methylpyridin-2-yl)-1H-imidazol-2-amine (83 mg, 61%) as a yellow solid. ¹H-NMR (400 MHz, DMSO-d₆): δ 11.3 and 11.1 (1H, two s), 8.81 (1H, d, J=6.8 Hz), 8.42 (1H, s), 8.17 (1H, s), 7.65 (1H, t, J=6.8 Hz), 7.51 (2H, t, J=7.0 Hz), 7.33-7.29 (2H, m), 7.22-7.17 (2H, m), 7.11 (1H, d, J=8.0 Hz), 6.59 and 6.38 (1H, two s), 4.57 (2H, d, J=6.4 Hz), 2.51 (3H, s). MS: 400.1 (M+H⁺).

Example 12

4-([1,2,4]triazolo[1,5-a]pyridin-7-yl)-N-(3-fluorobenzyl)-5-(6-methylpyridin-2-yl)-1H-imidazol-2ylamine

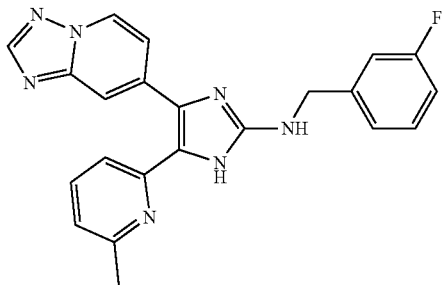 [SMILES: Cc1cccc(-c2[nH]c(NCc3cccc(F)c3)nc2-c2ccn3ncnc3c2)n1]

4-([1,2,4]triazolo[1,5-a]pyridin-2-yl)-5-(6-methylpyridin-2-yl)-1H-imidazol-2-amine (Intermediate 7, 100 mg, 0.343 mmol) was reacted with 3-fluorobenzaldehyde (0.0470 mL, 0.446 mmol) under the condition of Example 11. The crude product was purified by column chromatography on NH—SiO₂ (EtOAc only) to afford 4-([1,2,4]triazolo[1,5-a]pyridin-7-yl)-N-(3-fluorobenzyl)-5-(6-methylpyridin-2-yl)-1H-imidazol-2ylamine (99 mg, 73%) as a yellow solid. ¹H-NMR (400 MHz, CD₃OD): δ 8.65 (1H, brs), 8.35 (1H, s), 7.93 (1H, brs), 7.63 (1H, brs), 7.37-7.32 (2H, m), 7.24 (2H, d, J=7.2 Hz), 7.17 (2H, d, J=10.8 Hz), 6.98 (1H, t, J=9.0 Hz), 4.58 (2H, s), 2.51 (3H, s). MS: 400.3 (M+H⁺).

Example 13

4-([1,2,4]triazolo[1,5-a]pyridin-7-yl)-N-(3-chlorobenzyl)-5-(6-methylpyridin-2-yl)-1H-imidazol-2-amine

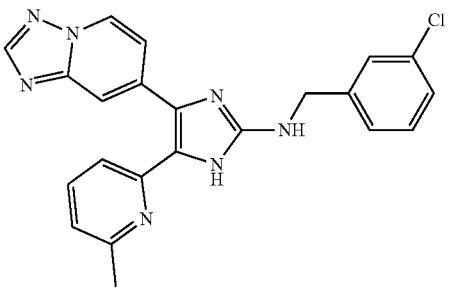 [SMILES: Cc1cccc(-c2[nH]c(NCc3cccc(Cl)c3)nc2-c2ccn3ncnc3c2)n1]

4-([1,2,4]triazolo[1,5-a]pyridine-7-yl)-5-(6-methylpyridin-2-yl)-1H-imidazol-2-amine (Intermediate 7, 40 mg, 0.137 mmol) was reacted with 3-chlorobenzaldehyde (25 mg, 0.179 mmol) under the condition of Example 11. The crude product was purified by column chromatography on NH—SiO₂ (EtOAc only) to afford 4-([1,2,4]triazolo[1,5-a]pyridin-7-yl)-N-(3-chlorobenzyl)-5-(6-methylpyridin-2-yl)-1H-imidazol-2-amine (28 mg, 50%) as a yellow solid. ¹H-NMR (400 MHz, MeOH-d₄): δ 8.64 (1H, d, J=6.8 Hz), 8.35 (1H, s), 7.89 (1H, brs), 7.65 (1H, t, J=8.0 Hz), 7.46 (1H, s), 7.37-7.28 (4H, m), 7.25 (1H, d, J=8.0 Hz), 7.17 (1H, d, J=7.2 Hz), 4.56 (2H, s), 2.51 (3H, s). MS: 416.00 (M+H⁺).

Example 14

4-([1,2,4]triazolo[1,5-a]pyridin-7-yl)-N-(4-chlorobenzyl)-5-(6-methylpyridin-2-yl)-1H-imidazol-2-amine

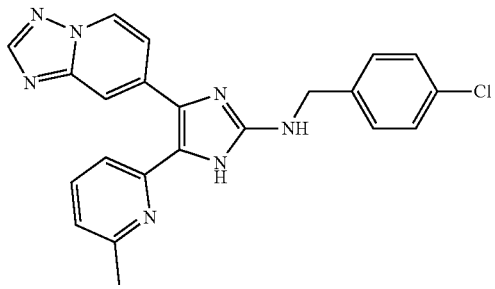 [SMILES: Cc1cccc(-c2[nH]c(NCc3ccc(Cl)cc3)nc2-c2ccn3ncnc3c2)n1]

4-([1,2,4]triazolo[1,5-a]pyridine-7-yl)-5-(6-methylpyridin-2-yl)-1H-imidazol-2-amine (Intermediate 7, 40 mg, 0.137 mmol) was reacted with 4-chlorobenzaldehyde (25 mg, 0.179 mmol) under the conditions of Example 11. The crude product was purified by column chromatography on NH—SiO$_2$ (EtOAc only) to afford 4-([1,2,4]triazolo[1,5-a]pyridin-7-yl)-N-(4-chlorobenzyl)-5-(6-methylpyridin-2-yl)-1H-imidazol-2-amine (20 mg, 35%) as a yellow solid. $^1$H-NMR (400 MHz, MeOH-d$_4$): δ 8.64 (1H, d, J=6.0 Hz), 8.35 (1H, s), 7.89 (1H, brs), 7.64 (1H, brs), 7.42 (2H, d, J=8.4 Hz), 7.35-7.22 (4H, m), 7.16 (1H, d, J=6.8 Hz), 4.55 (2H, s), 2.51 (3H, s). MS: 416.1 (M+H$^+$).

Example 15

4-([1,2,4]triazolo[1,5-a]pyridin-7-yl)-N-(2,3-difluorobenzyl)-5-(6-methylpyridin-2-yl)-1-imidazol-2-ylamine

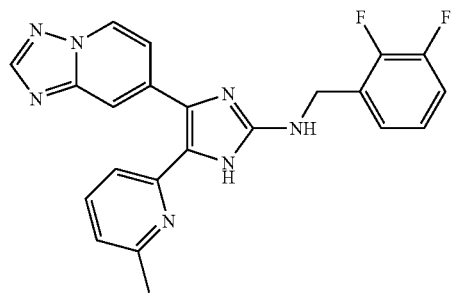 [SMILES: Cc1cccc(-c2[nH]c(NCc3cccc(F)c3F)nc2-c2ccn3ncnc3c2)n1]

4-([1,2,4]triazolo[1,5-a]pyridine-7-yl)-5-(6-methylpyridin-2-yl)-1H-imidazol-2-amine (Intermediate 7, 100 mg, 0.343 mmol) was reacted with 2,3-difluorobenzaldehyde (0.0490 mL, 0.446 mmol) under the conditions of Example 11. The crude product was purified by column chromatography on NH—SiO$_2$ (EtOAc only) to afford 4-([1,2,4]triazolo[1,5-a]pyridin-7-yl)-N-(2,3-difluorobenzyl)-5-(6-methylpyridin-2-yl)-1H-imidazol-2-ylamine (115 mg, 80%) as a yellow solid. $^1$H-NMR (400 MHz, CD$_3$OD): 6.8.64 (1H, s), 8.35 (1H, s), 7.92 (1H, brs), 7.63 (1H, brs), 7.38-7.29 (3H, m), 7.20-7.12 (3H, m), 4.67 (2H, s), 2.51 (3H, s). MS: 418.2 (M+H$^+$).

Example 16

4-([1,2,4]triazolo[1,5-a]pyridin-7-yl)-N-(2,6-difluorobenzyl)-5-(6-methylpyridin-2-yl)-1H-imidazol-2-amine

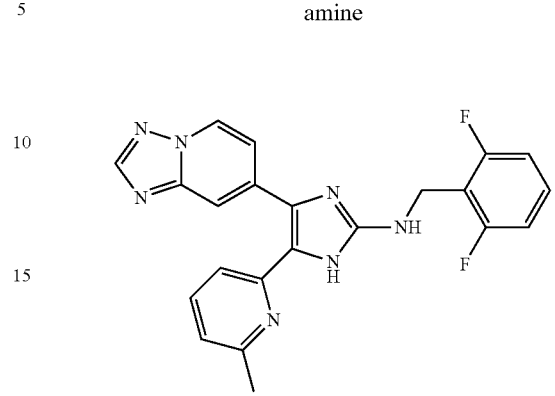

4-([1,2,4]triazolo[1,5-a]pyridin-7-yl)-5-(6-methylpyridin-2-yl)-1H-imidazol-2-amine (Intermediate 7, 50 mg, 0.172 mmol) was reacted with 2,6-difluorobenzaldehyde (0.0240 mL, 0.223 mmol) under the conditions of Example 11. The crude product was purified by column chromatography on NH—SiO$_2$ (DCM only DCM:MeOH=100:1) to afford 4-([1,2,4]triazolo[1,5-a]pyridin-7-yl)-N-(2,6-difluorobenzyl)-5-(6-methylpyridin-2-yl)-1H-imidazol-2-amine (14 mg, 20%) as a yellow solid. $^1$H-NMR (CDCl$_3$, Varian 400 MHz): δ 8.55 (1H, d, J=7.2 Hz), 8.34 (1H, s), 8.05, (1H, s), 7.44-7.39 (2H, m), 7.35-7.32 (1H, m), 7.30-7.24 (1H, m), 6.96-6.92 (3H, m), 4.86 (1H, brs), 4.62 (2H, d, J=6.4 Hz), 2.56 (3H, s). MS: 418.0 (M+H$^+$).

Example 17

4-([1,2,4]triazolo[1,5-a]pyridin-7-yl)-N-(4-chloro-2-fluorobenzyl)-5-(6-methylpyridin-2-yl)-1H-imidazol-2-amine

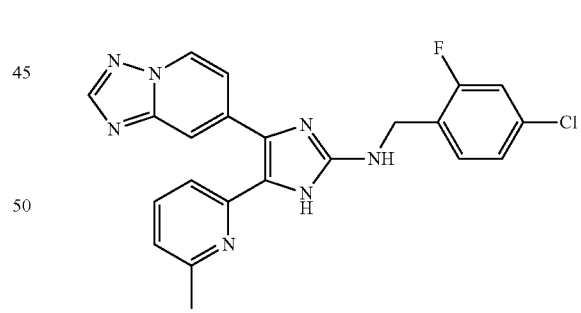

4-([1,2,4]triazolo[1,5-a]pyridin-7-yl)-5-(6-methylpyridin-2-yl)-1H-imidazol-2-amine (Intermediate 7, 50 mg, 0.172 mmol) was reacted with 5-chloro-2-fluorobenzaldehyde (35 mg, 0.223 mmol) under the conditions of Example 11. The crude product was purified by column chromatography on NH—SiO$_2$ (DCM:MeOH=100:1) to afford 4-([1,2,4]triazolo[1,5-a]pyridin-7-yl)-N-(4-chloro-2-fluorobenzyl)-5-(6-methylpyridin-2-yl)-1H-imidazol-2-amine (20 mg, 28%) as a yellow solid. $^1$H-NMR (400 MHz, DMSO-d$_6$): δ 11.4 and 11.2 (1H, s+s), 8.80 (1H, d, J=7.6 Hz), 8.42 (1H, s), 8.16 (1H, s), 7.65 (2H, t, J=10.0 Hz), 7.54-7.48 (2H, m), 7.42 (1H, dd, J=10.0, 2.0 Hz), 7.32-7.28 (1H, m), 7.11

(1H, d, J=7.6 Hz), 6.65 and 6.44 (1H, s+s), 4.53 (2H, d, J=6.0 Hz), 2.50 (3H, s). MS: 434.0 (M+H⁺).

Example 18

4-([1,2,4]triazolo[1,5-a]pyridin-7-yl)-N-(3-chloro-2-fluorobenzyl)-5-(6-methylpyridin-2-yl)-1H-imidazol-2-amine

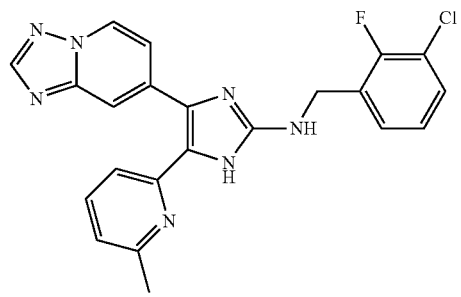 [SMILES: Cc1cccc(-c2[nH]c(NCc3cccc(Cl)c3F)nc2-c2ccn3ncnc3c2)n1]

4-([1,2,4]triazolo[1,5-a]pyridin-7-yl)-5-(6-methylpyridin-2-yl)-1H-imidazol-2-amine (Intermediate 7, 144 mg, 0.494 mmol) was reacted with 3-chloro-2-fluorobenzaldehyde (102 mg, 0.643 mmol) under the conditions of Example 11. The crude product was purified by column chromatography on NH—SiO₂ (EtOAc only) to afford 4-([1,2,4]triazolo[1,5-a]pyridin-7-yl)-N-(3-chloro-2-fluorobenzyl)-5-(6-methylpyridin-2-yl)-1H-imidazol-2-amine (58 mg, 27%) as a yellow solid. ¹H-NMR (400 MHz, CDCl₃): δ 9.52 (1H, brs), 8.55 (1H, d, J=7.2 Hz), 8.34 (1H, s), 8.06 (1H, s), 7.44-7.38 (3H, m), 7.35-7.31 (2H, m), 7.07 (1H, t, J=8.0 Hz), 6.94 (1H, d, J=8.0 Hz), 4.72 (1H, t, J=6.0 Hz), 4.63 (2H, d, J=6.4 Hz), 2.48 (3H, s). MS: 434.0 (M+H⁺).

Example 19

4-([1,2,4]triazolo[1,5-a]pyridin-7-yl)-N-(5-chloro-2-fluorobenzyl)-5-(6-methylpyridin-2-yl)-1H-imidazol-2-amine

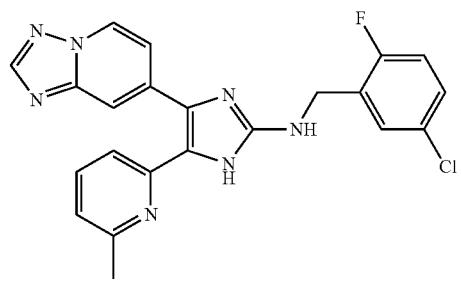 [SMILES: Cc1cccc(-c2[nH]c(NCc3cc(Cl)ccc3F)nc2-c2ccn3ncnc3c2)n1]

4-([1,2,4]triazolo[1,5-a]pyridine-7-yl)-5-(6-methylpyridin-2-yl)-1H-imidazol-2-amine (Intermediate 7, 50 mg, 0.172 mmol) was reacted with 5-chloro-2-fluorobenzaldehyde (35 mg, 0.223 mmol) under the conditions of Example 11. The crude product was purified by column chromatography on NH—SiO₂ (DCM:MeOH=100:1) to afford 4-([1,2,4]triazolo[1,5-a]pyridin-7-yl)-N-(5-chloro-2-fluorobenzyl)-5-(6-methylpyridin-2-yl)-1H-imidazol-2-amine (18 mg, 25%) as a yellow solid. ¹H-NMR (400 MHz, DMSO-d₆): δ 11.4 and 11.2 (1H, s+s), 8.81 (1H, d, J=7.2 Hz), 8.42 (1H, s,), 8.16 (1H, s), 7.66 (2H, t, J=7.4 Hz), 7.55 (1H, d, J=4.0 Hz), 7.49 (1H, d, J=7.2 Hz), 7.39-7.25 (2H, m), 7.12 (1H, d, J=7.2 Hz), 6.68 and 6.48 (1H, s+s), 4.54 (2H, d, J=6.0 Hz), 2.50 (3H, s). MS: 434.0 (M+H⁺).

Example 20

4-([1,2,4]triazolo[1,5-a]pyridin-7-yl)-N-(3,4-dichlorobenzyl)-5-(6-methylpyridin-2-yl)-1H-imidazol-2-amine

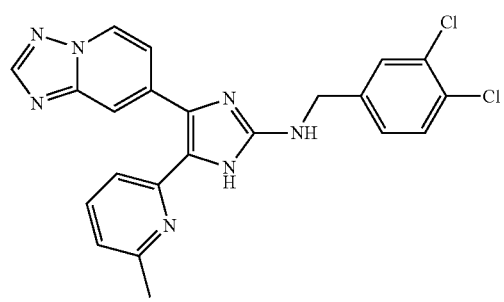 [SMILES: Cc1cccc(-c2[nH]c(NCc3ccc(Cl)c(Cl)c3)nc2-c2ccn3ncnc3c2)n1]

4-([1,2,4]triazolo[1,5-a]pyridin-7-yl)-5-(6-methylpyridin-2-yl)-1H-imidazol-2-amine (Intermediate 7, 40 mg, 0.137 mmol) was reacted with 3,4-dichlorobenzaldehyde (31 mg, 0.179 mmol) under the conditions of Example 11. The crude product was purified by column chromatography on NH—SiO₂ (EtOAc only) to afford 4-([1,2,4]triazolo[1,5-a]pyridin-7-yl)-N-(3,4-dichlorobenzyl)-5-(6-methylpyridin-2-yl)-1H-imidazol-2-amine (1.9 mg, 3.1%) as a yellow solid. ¹H-NMR (400 MHz, CD₃OD): 8.64 (1H, d, J=7.0 Hz), 8.35 (1H, s), 7.89 (1H, s), 7.65 (1H, t, J=7.4 Hz), 7.60 (1H, d, J=1.6 Hz), 7.48 (1H, d, J=8.4 Hz), 7.36 (1H, dd, J=8.4, 2.0 Hz), 7.36-7.32 (m, 2H), 7.17 (1H, d, J=7.6 Hz), 4.55 (2H, s), 2.51 (3H, s). MS: 450.0 (M+H⁺).

Example 21

4-([1,2,4]triazolo[1,5-a]pyridin-7-yl)-N-(2,4-dichlorobenzyl)-5-(6-methylpyridin-2-yl)-1H-imidazol-2-amine

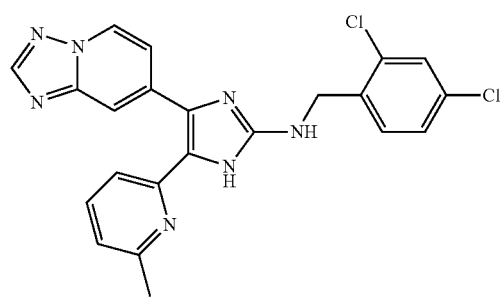 [SMILES: Cc1cccc(-c2[nH]c(NCc3ccc(Cl)cc3Cl)nc2-c2ccn3ncnc3c2)n1]

4-([1,2,4]triazolo[1,5-a]pyridin-7-yl)-5-(6-methylpyridin-2-yl)-1H-imidazol-2-amine (Intermediate 7, 40 mg, 0.137 mmol) was reacted with 2,4-dichlorobenzaldehyde (31 mg, 0.179 mmol) under the conditions of Example 11. The crude product was purified by column chromatography on NH—SiO₂ (EtOAc only) to afford 4-([1,2,4]triazolo[1,5-a]pyridin-7-yl)-N-(2,4-dichlorobenzyl)-5-(6-methylpyridin-2-yl)-1H-imidazol-2-amine (14 mg, 22%) as a yellow solid. ¹H-NMR (400 MHz, CD₃OD): 8.64 (1H, d, J=6.4 Hz), 8.35 (1H, s), 7.90 (1H, brs), 7.63 (1H, brs), 7.53 (1H, d, J=8.8 Hz), 7.48 (1H, d, J=2.0 Hz), 7.40-7.24 (2H, m), 7.32 (1H, dd, J=8.0, 2.4 Hz), 7.16 (1H, d, J=7.6 Hz), 4.64 (2H, s), 2.51 (3H, s). MS: 450.0 (M+H⁺).

Example 22

4-([1,2,4]triazolo[1,5-a]pyridin-7-yl)-N-(2-fluoro-3-methoxybenzyl)-5-(6-methylpyridin-2-yl)-1H-imidazol-2-amine

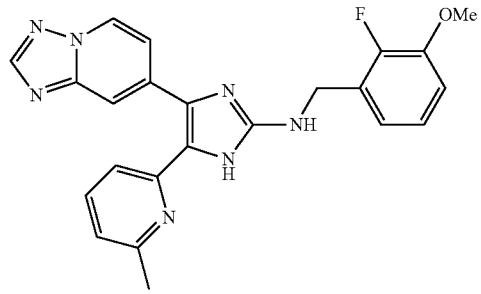 [SMILES: COc1cccc(CNc2nc(-c3ccn4ncnc4c3)c(-c3cccc(C)n3)[nH]2)c1F]

4-([1,2,4]triazolo[1,5-a]pyridin-7-yl)-5-(6-methylpyridin-2-yl)-1H-imidazol-2-amine (Intermediate 7, 50 mg, 0.172 mmol) was reacted with 2-fluoro-3methoxybenzaldehye (34 mg, 0.223 mmol) under the conditions of Example 11. The crude product was purified by column chromatography on NH—SiO₂ (EtOAc:MeOH=100:1) to afford 4-([1,2,4]triazolo[1,5-a]pyridin-7-yl)-N-(2-fluoro-3-methoxybenzyl)-5-(6-methylpyridin-2-yl)-1H-imidazol-2-amine (8.6 mg, 12%) as a yellow solid. ¹H-NMR (400 MHz, DMSO-d₆): 11.3 and 11.1 (1H, s+s), 8.81 (1H, d, J=7.6 Hz), 8.42 (1H, s), 8.16 (1H, s), 7.68-7.62 (1H, m), 7.49 (1H, dd, J=7.2, 1.6 Hz), 7.31 (1H, d, J=7.6 Hz), 7.12-7.03 (4H, m), 6.57 and 6.36 (1H, t+t, J=6.2 Hz), 4.55 (2H, d, J=6.4 Hz), 3.83 (3H, s), 2.50 (3H, s). MS: 430.1 (M+H⁺).

Example 23

4-([1,2,4]triazolo[1,5-a]pyridin-7-yl)-N-(2-fluoro-4-methoxybenzyl)-5-(6-methylpyridin-2-yl)-1H-imidazol-2-amine

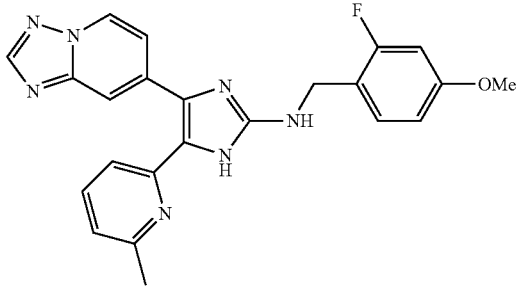 [SMILES: COc1ccc(CNc2nc(-c3ccn4ncnc4c3)c(-c3cccc(C)n3)[nH]2)c(F)c1]

4-([1,2,4]triazolo[1,5-a]pyridin-7-yl)-5-(6-methylpyridin-2-yl)-1H-imidazol-2-amine (Intermediate 7, 50 mg, 0.172 mmol) was reacted with 2-fluoro-4-methoxybenzaldehye (34 mg, 0.223 mmol) under the conditions of Example 11. The crude product was purified by column chromatography on NH—SiO₂ (EtOAc only) to afford the 4-([1,2,4]triazolo[1,5-a]pyridin-7-yl)-N-(2-fluoro-4-methoxybenzyl)-5-(6-methylpyridin-2-yl)-1H-imidazol-2-amine (10 mg, 14%) as a yellow solid. ¹H-NMR (400 MHz, DMSO-d₆): 11.3 and 11.1 (1H, s+s), 8.81 (1H, d, J=7.2 Hz), 8.42 (1H, s), 8.17 (1H, s), 7.71-7.62 (1H, m), 7.51 (1H, dd, J=7.4, 1.8 Hz), 7.42 (1H, t, J=9.0 Hz), 7.31 (1H, d, J=8.0 Hz), 7.11 (1H, d, J=7.2 Hz), 6.82 (1H, d, J=11.2 Hz), 6.78 (1H, d, J=8.0 Hz), 6.48 and 6.26 (1H, t+t, J=6.4 Hz), 4.46 (2H, d, J=5.2 Hz), 3.74 (3H, s), 2.50 (3H, s). MS: 430.1 (M+H⁺).

Example 24

3-((4-([1,2,4]triazolo[1,5-a]pyridin-7-yl)-5-(6-methylpyridin-2-yl)-1H-imidazol-2ylamino)methyl)-N-methylbenzamide

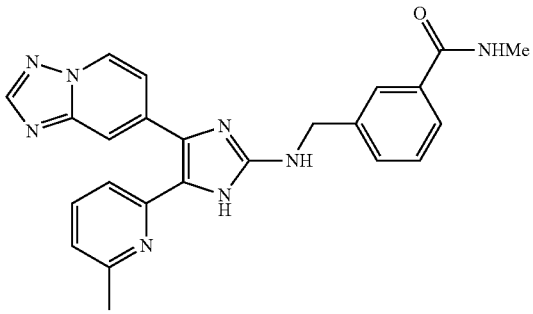 [SMILES: CNC(=O)c1cccc(CNc2nc(-c3ccn4ncnc4c3)c(-c3cccc(C)n3)[nH]2)c1]

4-(1-methyl-1H-benzo[d][1,2,3]triazol-6-yl)-5-(6-methylpyridin-2-yl)-1H-imidazol-2-amine (Intermediate 7, 137 mg, 0.471 mmol) was reacted with 3-formyl-N-methylbenzamide (100 mg, 0.613 mmol) under the conditions of Example 11. The crude product was purified by column chromatography on NH—SiO₂ (EtOAc to EtOAc: MeOH=100:1) to afford 3-((4-([1,2,4]triazolo[1,5-a]pyridin-7-yl)-5-(6-methylpyridin-2-yl)-1H-imidazol-2ylamino) methyl)-N-methylbenzamide (32 mg, 16%) as a yellow solid. ¹H-NMR (400 MHz, CD₃OD): δ 8.64 (1H, d, J=6.8 Hz), 8.35 (1H, s), 7.89 (2H, s), 7.69 (1H, d, J=8.0 Hz), 7.66-7.62 (1H, m), 7.61 (1H, d, J=8.0 Hz), 7.44 (1H, t, J=7.8 Hz), 7.32 (2H, brs), 7.44 (1H, t, J=7.8 Hz), 4.62 (2H, s), 2.91 (3H, s), 2.50 (3H, s). MS: 439.1 (M+H⁺).

Example 25

4-((4-([1,2,4]triazolo[1,5-a]pyridin-7-yl)-5-(6-methylpyridin-2-yl)-1H-imidazol-2-ylamino)methyl)-N-methylbenzamide

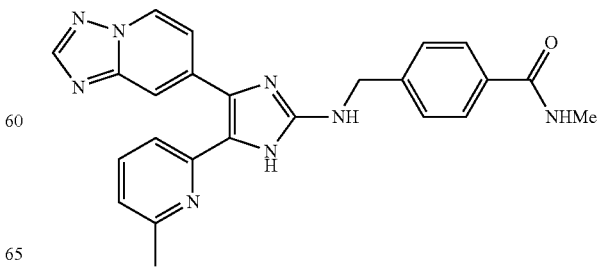

4-(1-methyl-1H-benzo[d][1,2,3]triazol-6-yl)-5-(6-methylpyridin-2-yl)-1H-imidazol-2-amine (Intermediate 7, 125 mg, 0.429 mmol) was reacted with 4-formyl-N-methylbenzamide (70 mg, 0.429 mmol) under the conditions of Example 11. The crude product was purified by column chromatography on NH—SiO$_2$ (DCM:MeOH=50:1) to afford 4-((4-([1,2,4]triazolo[1,5-a]pyridin-7-yl)-5-(6-methylpyridin-2-yl)-1H-imidazol-2-ylamino)methyl)-N-methylbenzamide (2.4 mg, 1.3%) as a yellow solid. $^1$H-NMR (400 MHz, CD$_3$OD): δ 8.83 (1H, d, J=7.2 Hz), 8.49 (1H, s), 8.00 (1H, s), 7.85 (2H, d, J=8.0 Hz), 7.70 (1H, t, J=8.0 Hz), 7.54 (2H, d, J=8.4 Hz), 7.35-7.25 (3H, m), 4.74 (2H, s), 2.91 (3H, s), 2.56 (3H, s). MS: 439.1 (M+H$^+$).

Example 26

N-(4-([1,2,4]triazolo[1,5-a]pyridin-7-yl)-5-(6-methylpyridin-2-yl)-1H-imidazol-2-yl)-2-fluorobenzamide

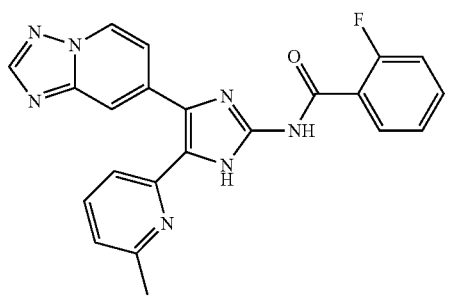 [SMILES: Cc1cccc(-c2[nH]c(NC(=O)c3ccccc3F)nc2-c2ccn3ncnc3c2)n1]

To a solution of 4-([1,2,4]triazolo[1,5-a]pyridin-7-yl)-5-(6-methylpyridin-2-yl)-1H-imidazol-2-amine (Intermediate 7, 80 mg, 0.275 mmol) in DCM (2.8 mL) was added 2-fluorobenzoyl chloride (44 mg, 0.275 mmol) and TEA (0.080 mL, 0.549 mmol) at room temperature. After stirred for 3 hours at room temperature, the reaction mixture was diluted with water and extracted with DCM twice. The combined organic layers were washed with water and brine, dried over Na$_2$SO$_4$, filtered and concentrated in vacuo. The residue was purified by column chromatography on NH—SiO$_2$ (EtOAc only to EtOAc:MeOH=10:1) to afford N-(4-([1,2,4]triazolo[1,5-a]pyridin-7-yl)-5-(6-methylpyridin-2-yl)-1H-imidazol-2-yl)-2-fluorobenzamide (24 mg, 22%) as a pale yellow solid. $^1$H-NMR (400 MHz, CDCl$_3$): δ 11.60 (1H, brs), 9.82 (1H, brs), 8.57 (1H, d, J=6.8 Hz), 8.36 (1H, s), 8.16 (1H, t, J=7.8 Hz), 8.08 (1H, s), 7.60-7.56 (1H, m), 7.49 (1H, t, J=7.4 Hz), 7.40-7.31 (3H, m), 7.21 (1H, t, J=10.0 Hz), 7.06 (1H, d, J=7.6 Hz), 2.63 (3H, s). MS: 414.2 (M+H$^+$).

Example 27

4-([1,2,4]tiazolo[1,5-a]pyridin-7-yl)-N-(1-(2-fluorophenyl)ethyl)-5-(6-methylpyridin-2-yl)-1H-imidazol-2-amine

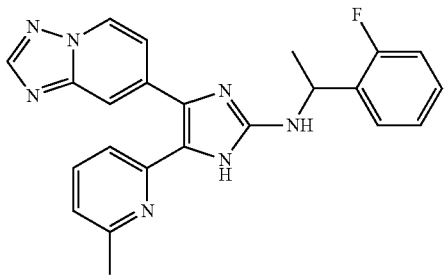 [SMILES: Cc1cccc(-c2[nH]c(NC(C)c3ccccc3F)nc2-c2ccn3ncnc3c2)n1]

A mixture of 4-([1,2,4]triazolo[1,5-a]pyridin-7-yl)-5-(6-methylpyridin-2-yl)-1H-imidazol-2-amine (Intermediate 7, 100 mg, 0.343 mmol), 2-fluorobenzaldehyde (0.0500 mL, 0.446 mmol), and K$_2$CO$_3$ (95.0 mg, 0.687 mmol) in MeOH (3.4 mL) was stirred at room temperature for 18 hours. After filtered through a Celite pad, the filtrate was concentrated in vacuo. The residue was dissolved dry THF (3.4 mL). After addition of ZnCl$_2$ (4.68 mg, 0.034 mmol) and methylmagnesium chloride (3.0 M solution in THF, 0.34 mL, 1.03 mmol) at 0° C., the reaction mixture was stirred at room temperature for 1 hour and then quenched with saturated aq. NH$_4$Cl. The mixture was extracted with DCM twice. The combined organic layers were washed with water and brine, dried over Na$_2$SO$_4$, filtered and concentrated in vacuo. The residue was purified by column chromatography on NH$_2$—SiO$_2$ (Hexanes:EtOAc=1:3) to afford 4-([1,2,4]tiazolo[1,5-a]pyridin-7-yl)-N-(1-(2-fluorophenyl)ethyl)-5-(6-methylpyridin-2-yl)-1H-imidazol-2-amine (40 mg, 28%) as a yellow solid. $^1$H-NMR (400 MHz, CDCl$_3$): δ 9.65 (1H, brs), 8.53 (1H, d, J=6.8 Hz), 8.33 (1H, s), 8.04 (1H, s), 7.45 (1H, td, J=7.6, 1.6 Hz), 7.41-7.38 (2H, m), 7.30 (1H, d, J=9.2 Hz), 7.24 (1H, d, J=6.0 Hz), 7.14 (1H, t, J=7.2 Hz), 7.06 (1H, t, J=9.4 Hz), 6.90 (1H, d, J=7.6 Hz), 5.02 (1H, quint, J=6.8 Hz), 4.87 (1H, d, J=6.8 Hz), 2.37 (3H, s), 1.57 (3H, d, J=6.8 Hz). MS: 414.1 (M+H$^+$).

Biological Activity

Cell Culture

Human cancer cell lines Hs578T (ATCC® HTB-22™) cells were grown in DMEM (Dulbecco's modified Eagle's medium) supplemented with 10% fetal bovine serum and 1% mixture of penicillin and streptomycin (Gibco). Cells were maintained at 37° C. in a humidified 5% CO$_2$ atmosphere.

ALK5 Kinase Assay

Recombinant ALK5 proteins, ATP and ALK5 substrate (Promega, Madison, USA) at final concentrations of 25 ng, 50 μM and 0.2 ug/ul, respectively, were aliquoted in 50 ul kinase buffer supplemented with 50 uM DTT into 96-well plates, in combination with inhibitor compounds diluted at varying concentrations in kinase buffer in triplicate. Positive control samples lacking inhibitor compounds and negative controls lacking recombinant kinase were also measured in triplicate. The mixture was reacted at RT for 120 min. 50 ul ADP-Glo reagent (Promega) was added and incubate at RT for 40 min. and then 100 ul of kinase detection reagent was added and incubate at RT for 30 min. Kinase activities were measured by Varioskan LUX multimode microplate reader (Thermo Fisher Scientific, Waltham, USA). SigmaPlot (Systat software) was used for graphing and regression analysis by sigmoidal dose-response with variable Hill coefficient.

Cell-Based Luciferase Reporter Assay for ALK5 Activity

Biological activity of the compounds of BSC-1200 was determined by selectively inhibit with Smad 2/3-responsive promoter in response to TGF-β1 stimulation at cellular level. Cells were seeded at $3\times10^4$/well in 24-well plates were transiently transfected with 500 ng of (CAGA)-12-luciferase reporter construct and 5 ng of pRL-TK *Renilla* luciferase vector (Promega, Madison, WI), an internal control for transfection efficiency, using Lipofectamine 3000 reagent (Thermo Fisher Scientific, Waltham, USA). After 24 h transfection, the cells were pre-treated with ALK5 inhibitor in dose-dependent manner. And then, Cells stimulated with 2 ng/ml recombinant TGF-β1 for 12 hours. After the stimulation, the firefly and *Renilla* luciferase activities were measured by Dual-Luciferase Repoter Assay (Promega).

Phospho-Smad 2/3 Immunoblotting

Biological activity of the compounds of BSC-1200 was determined by measuring their ability to inhibit TGF-β induced phosphor-Smad 2/3 levels in Hs578T cells. Cells were pretreated with ALK5 inhibitors (10, 20, 50, 100 nM) for 1 h and treated with human recombinant 2 ng/ml TGF-β1 for 1 h under serum free. Cells were lysed in a buffer containing mM HEPES, pH 7.6, 150 mM NaCl, 1% NP40, 1% sodium deoxycholate, 0.1% SDS, and protease inhibitor mixture (Bimake, Houston, USA). Extracts were separated by SDS-PAGE followed by electro-transfer to polyvinylidene difloride (PVDF) membranes and probed with an anti-phospho-Smad 2 Ab, anti-phospho-Smad 3 Ab, anti-Smad 2/3 Ab and α-tubulin, followed by horseradish peroxidase-conjugated anti-rabbit, anti-mouse IgG and revealed with Super Signal® West dura kit (Pierce). The membranes are placed in an image analyzer (Imagequant LAS 500; GE Heathcare), connected to a computer which allows the image generation (Software Image Reader LAS 500).

Relative luciferase activity: $IC_{50}$ value (nM)

A: below 10 nM, B: 10-100 nM, C: above 100 nM

| Example | Structure | Compoud ID | Assay |
|---|---|---|---|
| 1 | 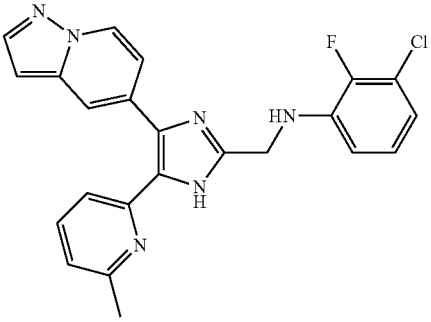 [SMILES: Cc1cccc(-c2[nH]c(CNc3cccc(Cl)c3F)nc2-c2ccn3nccc3c2)n1] | 50 | B |
| 2 | 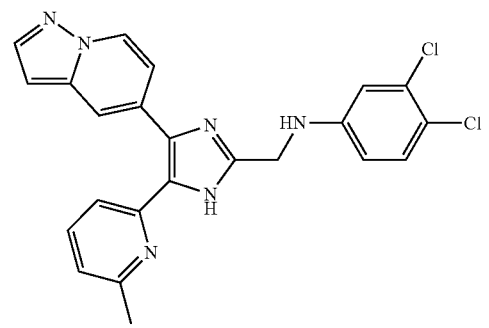 [SMILES: Cc1cccc(-c2[nH]c(CNc3ccc(Cl)c(Cl)c3)nc2-c2ccn3nccc3c2)n1] | 51 | A |
| 3 | 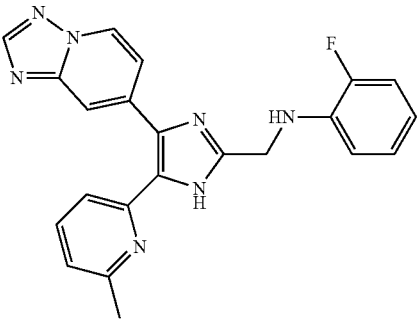 [SMILES: Cc1cccc(-c2[nH]c(CNc3ccccc3F)nc2-c2ccn3ncnc3c2)n1] | 8 | B |

-continued
| Example | Structure | Compoud ID | Assay |
|---|---|---|---|
| 4 | 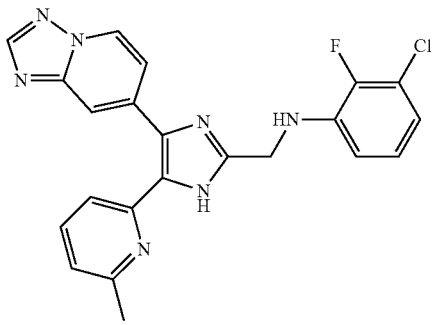 [SMILES: Cc1cccc(-c2[nH]c(CNc3cccc(Cl)c3F)nc2-c2ccn3ncnc3c2)n1] | 46 | A |
| 5 | 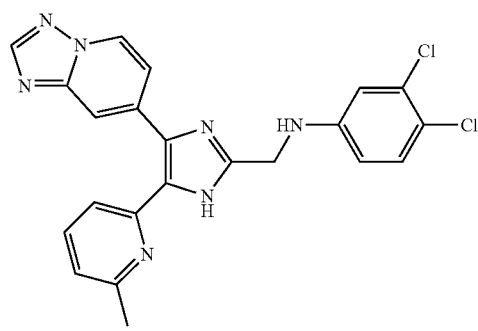 [SMILES: Cc1cccc(-c2[nH]c(CNc3ccc(Cl)c(Cl)c3)nc2-c2ccn3ncnc3c2)n1] | 47 | A |
| 6 | 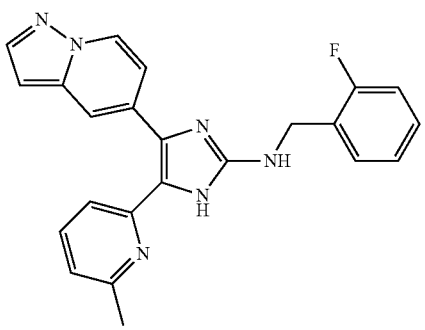 [SMILES: Cc1cccc(-c2[nH]c(NCc3ccccc3F)nc2-c2ccn3nccc3c2)n1] | 24 | B |
| 7 | 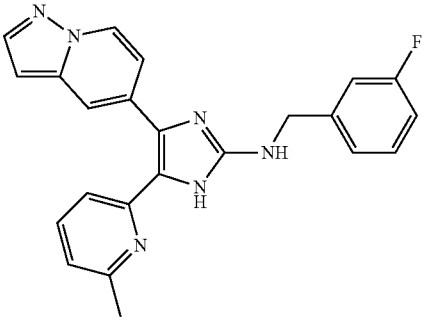 [SMILES: Cc1cccc(-c2[nH]c(NCc3cccc(F)c3)nc2-c2ccn3nccc3c2)n1] | 53 | B |

-continued
| Example | Structure | Compoud ID | Assay |
|---|---|---|---|
| 8 | 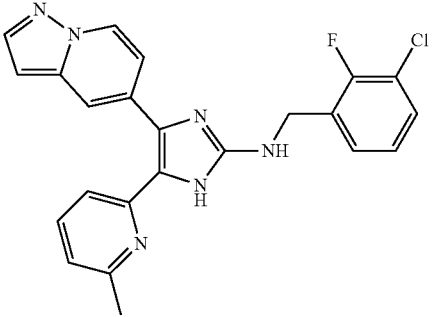 [SMILES: Cc1cccc(-c2[nH]c(NCc3cccc(Cl)c3F)nc2-c2ccn3nccc3c2)n1] | 42 | B |
| 9 | 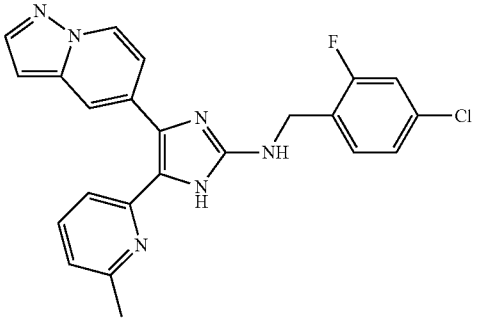 [SMILES: Cc1cccc(-c2[nH]c(NCc3ccc(Cl)cc3F)nc2-c2ccn3nccc3c2)n1] | 29 | A |
| 10 | 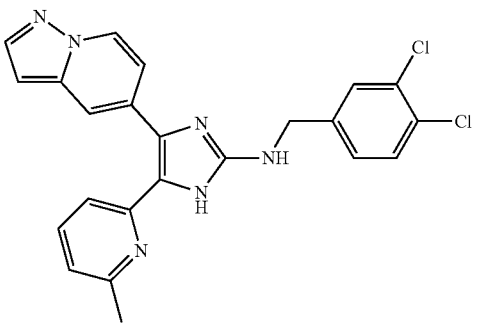 [SMILES: Cc1cccc(-c2[nH]c(NCc3ccc(Cl)c(Cl)c3)nc2-c2ccn3nccc3c2)n1] | 43 | B |
| 11 | 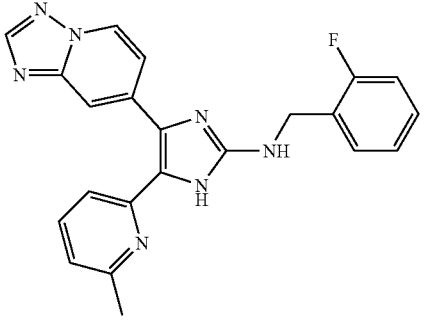 [SMILES: Cc1cccc(-c2[nH]c(NCc3ccccc3F)nc2-c2ccn3ncnc3c2)n1] | 15 | B |

-continued

| Example | Structure | Compoud ID | Assay |
|---|---|---|---|
| 12 | 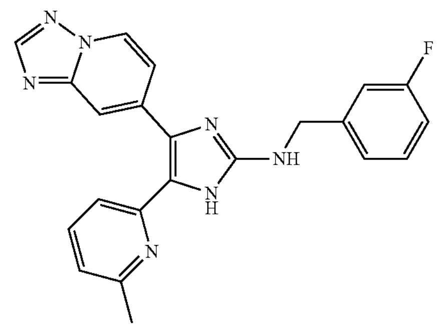 [SMILES: Cc1cccc(-c2[nH]c(NCc3cccc(F)c3)nc2-c2ccn3ncnc3c2)n1] | 52 | B |
| 13 | 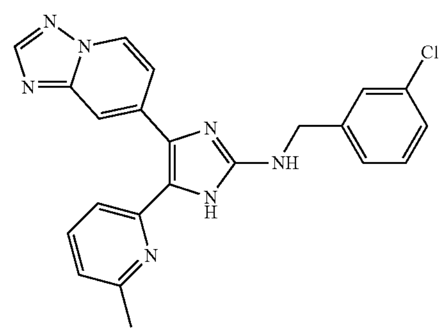 [SMILES: Cc1cccc(-c2[nH]c(NCc3cccc(Cl)c3)nc2-c2ccn3ncnc3c2)n1] | 31 | B |
| 14 | 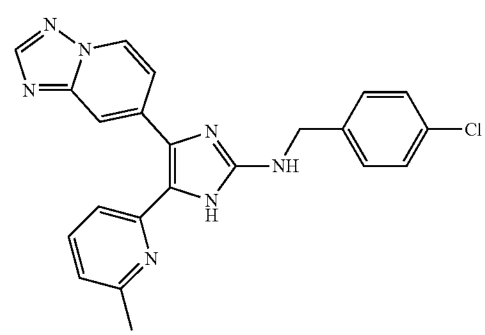 [SMILES: Cc1cccc(-c2[nH]c(NCc3ccc(Cl)cc3)nc2-c2ccn3ncnc3c2)n1] | 32 | A |
| 15 | 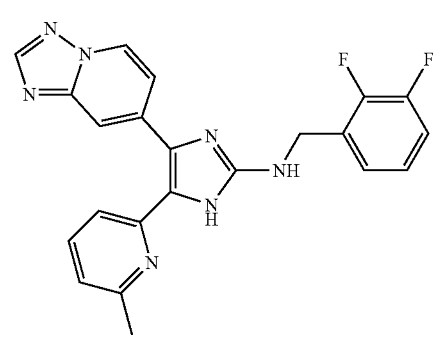 [SMILES: Cc1cccc(-c2[nH]c(NCc3cccc(F)c3F)nc2-c2ccn3ncnc3c2)n1] | 54 | B |

-continued

| Example | Structure | Compound ID | Assay |
|---|---|---|---|
| 16 | 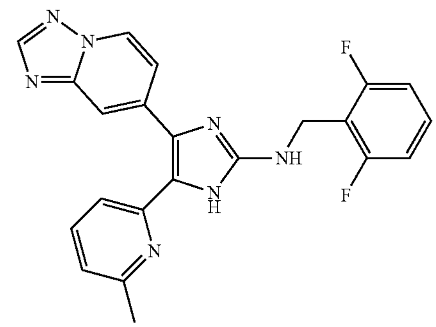 [SMILES: Cc1cccc(-c2[nH]c(NCc3c(F)cccc3F)nc2-c2ccn3ncnc3c2)n1] | 19 | B |
| 17 | 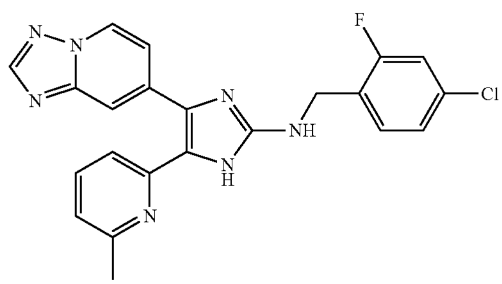 [SMILES: Cc1cccc(-c2[nH]c(NCc3ccc(Cl)cc3F)nc2-c2ccn3ncnc3c2)n1] | 23 | B |
| 18 | 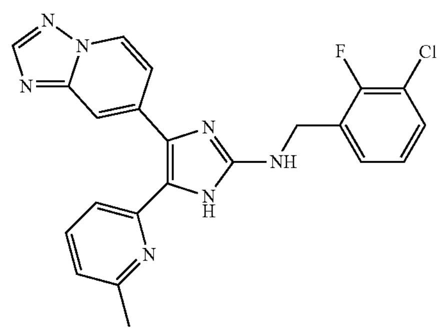 | 30 | A |
| 19 | 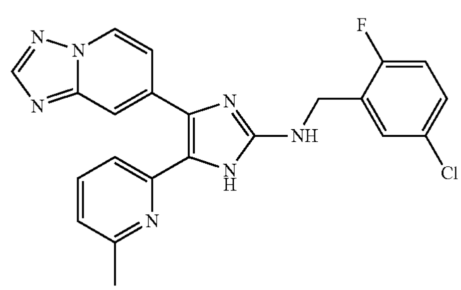 [SMILES: Cc1cccc(-c2[nH]c(NCc3cc(Cl)ccc3F)nc2-c2ccn3ncnc3c2)n1] | 22 | B |
| 20 | 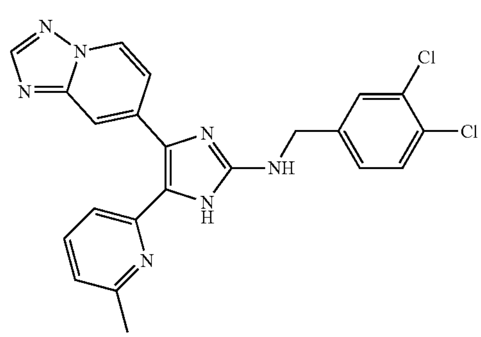 | 34 | A |

-continued
| Example | Structure | Compoud ID | Assay |
|---|---|---|---|
| 21 | 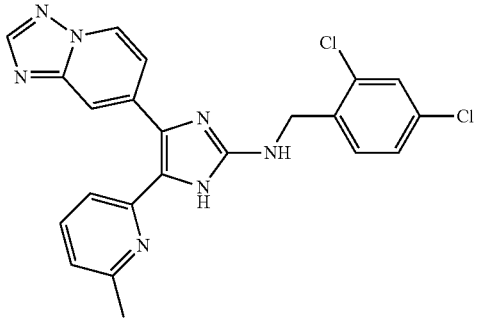 | 33 | B |
| 22 | 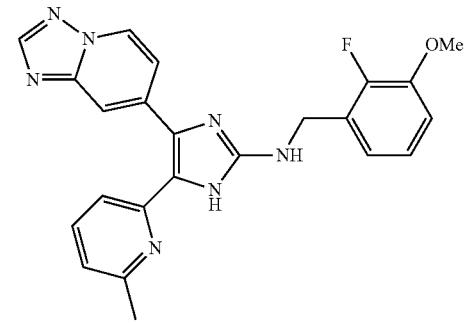 [SMILES: COc1cccc(CNc2nc(-c3ccn4ncnc4c3)c(-c3cccc(C)n3)[nH]2)c1F] | 35 | B |
| 23 | 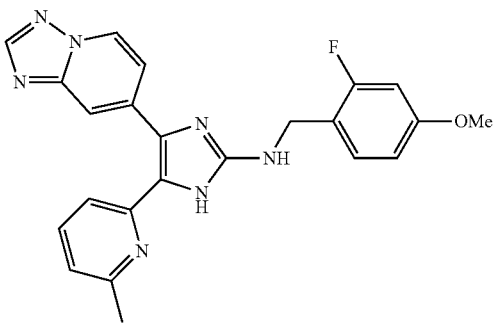 [SMILES: COc1ccc(CNc2nc(-c3ccn4ncnc4c3)c(-c3cccc(C)n3)[nH]2)c(F)c1] | 36 | B |
| 24 | 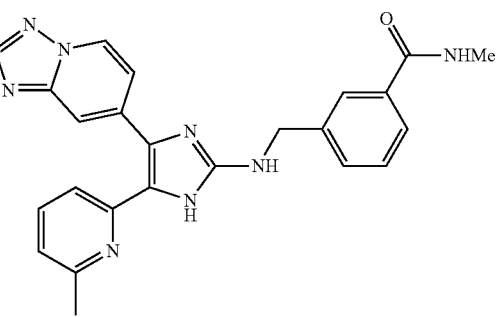 | 41 | C |
| 25 | 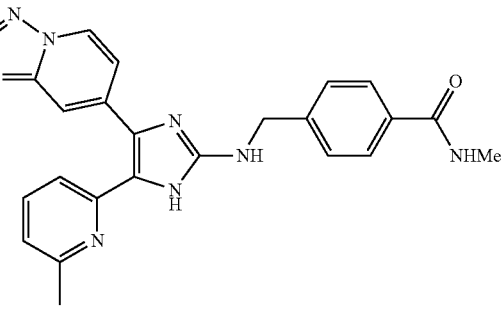 | 40 | C |

| Example | Structure | Compound ID | Assay |
|---|---|---|---|
| 26 | 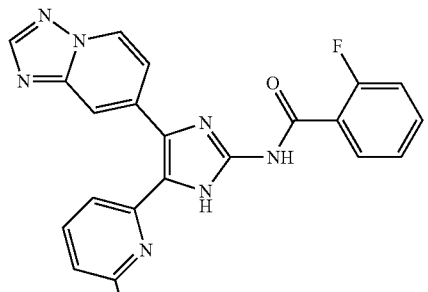 | 18 | B |
| 27 | 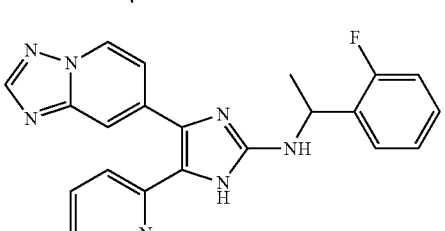 | 28 | B |

The invention claimed is:

1. A compound of Formula IIa, or a pharmaceutically acceptable salt thereof,

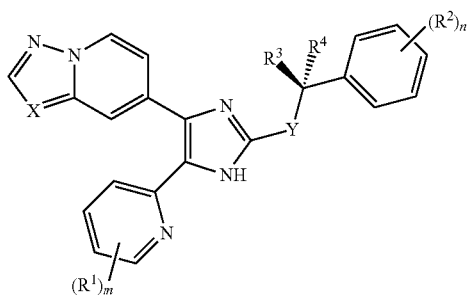

wherein
each $R^1$ is independently selected from the group consisting of hydrogen, halogen, $CF_3$, acyl, amino, substituted amino, $C_1$-$C_6$ alkyl, substituted $C_1$-$C_6$ alkyl, $C_1$-$C_6$ haloalkyl, $C_3$-$C_7$ cycloalkyl, alkylcarboxy, cyano, nitro, and alkoxy;
each $R^2$ is independently selected from the group consisting of hydrogen, halogen, $CF_3$, acyl, amino, substituted amino, $C_1$-$C_6$ alkyl, substituted $C_1$-$C_6$ alkyl, $C_1$-$C_6$ haloalkyl, cyano, nitro, alkoxy, acyloxy, and aryloxy;
m is 0, 1, 2, 3 or 4;
n is 0, 1, 2, 3, 4 or 5;
X is CH or N;
Y is NH, $NR^5$, O, S, S(O) or $S(O)_2$;
$R^3$ is selected from the group consisting of F, $CF_3$, $C_1$-$C_6$ alkyl, substituted $C_1$-$C_6$ alkyl, and cyano;
or $R^3$ and $R^4$ together with the atom to which they are attached form a 3 to 7 membered carbocyclic or heterocyclic ring;
$R^4$ is F, $CF_3$ or $C_1$-$C_6$ alkyl; and
$R^5$ is $C_1$-$C_6$ alkyl, $C_1$-$C_6$ fluoroalkyl, $C_1$-$C_6$ difluoroalkyl or $C_1$-$C_6$ trifluoroalkyl.

2. A pharmaceutical composition comprising a pharmaceutically effective amount of the compound of claim 1 or the pharmaceutically acceptable salt thereof.

3. A method for inhibiting an activin receptor like kinase 5 (ALK5) enzyme, comprising the step of contacting the ALK5 enzyme with an amount sufficient to inhibit the enzyme of the compound of claim 1 or the pharmaceutically acceptable salt thereof.

4. A method for the treatment of an ALK5 mediated disease or condition, comprising administering to a subject in need thereof a pharmaceutically effective amount of a composition comprising the compound of claim 1 or the pharmaceutically acceptable salt thereof, wherein the disease or condition is selected from the group consisting of papillary thyroid carcinoma, pancreatic cancer, lung cancer, colon cancer, breast carcinoma, and neuroblastoma.

5. The compound of claim 1, wherein the compound is selected from the group consisting of:
N-(2-fluorobenzyl)-5-(6-methylpyridin-2-yl)-4-(pyrazolo[1,5-a]pyridine-5-yl)-1H-imidazol-2-amine;
N-(3-fluorobenzyl)-5-(6-methylpyridin-2-yl)-4-(pyrazolo[1,5-a]pyridine-5-yl)-1H-imidazol-2-amine;
N-(3-chloro-2-fluorobenzyl)-5-(6-methylpyridin-2-yl)-4-(pyrazolo[1,5-a]pyridine-5-yl)-1H-imidazol-2-amine;
N-(4-chloro-2-fluorobenzyl)-5-(6-methylpyridin-2-yl)-4-(pyrazolo[1,5-a]pyridine-5-yl)-1H-imidazol-2-amine;
N-(3,4-dichlorobenzyl)-5-(6-methylpyridin-2-yl)-4-(pyrazolo[1,5-a]pyridine-5-yl)-1H-imidazol-2-amine;
4-([1,2,4]triazolo[1,5-a]pyridin-7-yl)-N-(2-fluorobenzyl)-5-(6-methylpyridin-2-yl)-1H-imidazol-2-amine;
4-([1,2,4]triazolo[1,5-a]pyridin-7-yl)-N-(3-fluorobenzyl)-5-(6-methylpyridin-2-yl)-1H-imidazol-2ylamine;
4-([1,2,4]triazolo[1,5-a]pyridin-7-yl)-N-(3-chlorobenzyl)-5-(6-methylpyridin-2-yl)-1H-imidazol-2-amine;

4-([1,2,4]triazolo[1,5-a]pyridin-7-yl)-N-(4-chlorobenzyl)-5-(6-methylpyridin-2-yl)-1H-imidazol-2-amine;

4-([1,2,4]triazolo[1,5-a]pyridin-7-yl)-N-(2,3-difluorobenzyl)-5-(6-methylpyridin-2-yl)-1H-imidazol-2-ylamine;

4-([1,2,4]triazolo[1,5-a]pyridin-7-yl)-N-(2,6-difluorobenzyl)-5-(6-methylpyridin-2-yl)-1H-imidazol-2-amine;

4-([1,2,4]triazolo[1,5-a]pyridin-7-yl)-N-(4-chloro-2-fluorobenzyl)-5-(6-methylpyridin-2-yl)-1H-imidazol-2-amine;

4-([1,2,4]triazolo[1,5-a]pyridin-7-yl)-N-(3-chloro-2-fluorobenzyl)-5-(6-methylpyridin-2-yl)-1H-imidazol-2-amine;

4-([1,2,4]triazolopyridin-7-yl)-N-(5-chloro-2-fluorobenzyl)-5-(6-methylpyridin-2-yl)-1H-imidazol-2-amine;

4-([1,2,4]triazolo[1,5-a]pyridin-7-yl)-N-(3,4-dichlorobenzyl)-5-(6-methylpyridin-2-yl)-1H-imidazol-2-amine;

4-([1,2,4]triazolo[1,5-a]pyridin-7-yl)-N-(2,4-dichlorobenzyl)-5-(6-methylpyridin-2-yl)-1H-imidazol-2-amine;

4-([1,2,4]triazolo[1,5-a]pyridin-7-yl)-N-(2-fluoro-3-methoxybenzyl)-5-(6-methylpyridin-2-yl)-1H-imidazol-2-amine;

4-([1,2,4]triazolo[1,5-a]pyridin-7-yl)-N-(2-fluoro-4-methoxybenzyl)-5-(6-methylpyridin-2-yl)-1H-imidazol-2-amine;

3-((4-([1,2,4]triazolo[1,5-a]pyridin-7-yl)-5-(6-methylpyridin-2-yl)-1H-imidazol-2ylamino)methyl)-N-methylbenzamide;

4-((4-([1,2,4]triazolo[1,5-a]pyridin-7-yl)-5-(6-methylpyridin-2-yl)-1H-imidazol-2-ylamino)methyl)-N-methylbenzamide;

4-([1,2,4]triazolo[1,5-a]pyridin-7-yl)-N-(1-(2-fluorophenyl)ethyl)-5-(6-methylpyridin-2-yl)-1H-imidazol-2-amine; and a pharmaceutically acceptable salt thereof.

\* \* \* \* \*